(12) United States Patent
Nolan et al.

(10) Patent No.: US 10,888,410 B2
(45) Date of Patent: Jan. 12, 2021

(54) STENT AND SLEEVE DEPLOYMENT

(71) Applicant: BOSTON SCIENTIFIC SCIMED, INC., Maple Grove, MN (US)

(72) Inventors: Damien Vincent Nolan, Galway (IE); Martyn G. Folan, Galway (IE); Martin Hynes, Galway (IE); Thomas Martin Keating, Galway (IE); Bryan Forde, Galway (IE); Kathleen Corcoran, Watertown, MA (US); Kevin M. Reavis, Portland, OR (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 51 days.

(21) Appl. No.: 16/008,689

(22) Filed: Jun. 14, 2018

(65) Prior Publication Data

US 2018/0360589 A1 Dec. 20, 2018

Related U.S. Application Data

(60) Provisional application No. 62/521,129, filed on Jun. 16, 2017.

(51) Int. Cl.
*A61F 2/04* (2013.01)
*A61F 2/966* (2013.01)
(Continued)

(52) U.S. Cl.
CPC ............ *A61F 2/04* (2013.01); *A61F 2/07* (2013.01); *A61F 2/90* (2013.01); *A61F 2/91* (2013.01);
(Continued)

(58) Field of Classification Search
CPC ........................................ A61F 2/04
See application file for complete search history.

(56) References Cited

U.S. PATENT DOCUMENTS

| 5,238,004 A | 8/1993 | Sahatjian et al. |
| 5,405,378 A | 4/1995 | Strecker |
| (Continued) | | |

FOREIGN PATENT DOCUMENTS

| EP | 2604232 A1 | 6/2013 |
| WO | 2015200554 A1 | 12/2015 |

OTHER PUBLICATIONS

International Search Report and Written Opinion dated Sep. 25, 2018 for International Application No. PCT/US2018/037571.

*Primary Examiner* — Matthew W Schall
(74) *Attorney, Agent, or Firm* — Seager, Tufte & Wickhem, LLP

(57) ABSTRACT

A delivery system for delivering an implant having both a rigid portion and a flexible portion to a body lumen. The delivery system includes an outer tubular member and an inner tubular member slidably disposed within the lumen of the outer tubular member. The inner tubular member includes at least one opening positioned in a side wall adjacent to a distal end region. An expandable implant, including a rigid portion and a flexible portion, is disposed about the outer surface of the inner tubular member. A distal portion of a thread is wrapped around the flexible portion of the implant and configured to maintain the flexible portion in a radially collapsed configuration during delivery of the implant. A distal end region of the outer tubular member is disposed around the rigid portion of the implant to maintain the rigid portion in a radially collapsed configuration during delivery of the implant.

20 Claims, 20 Drawing Sheets

(51) Int. Cl.
  *A61F 2/07* (2013.01)
  *A61F 2/90* (2013.01)
  *A61F 2/91* (2013.01)
  *A61F 2/962* (2013.01)
  *A61F 2/95* (2013.01)

(52) U.S. Cl.
  CPC .............. *A61F 2/962* (2013.01); *A61F 2/966* (2013.01); *A61F 2/9517* (2020.05); *A61F 2002/044* (2013.01); *A61F 2002/045* (2013.01); *A61F 2002/072* (2013.01); *A61F 2002/9511* (2013.01); *A61F 2002/9665* (2013.01); *A61F 2210/0014* (2013.01); *A61F 2250/0018* (2013.01); *A61F 2250/0039* (2013.01)

(56) References Cited

U.S. PATENT DOCUMENTS

| | | | |
|---|---|---|---|
| 5,653,746 A | 8/1997 | Schmitt | |
| 5,941,855 A | 8/1999 | Picha et al. | |
| 5,948,191 A | 9/1999 | Solovay | |
| 6,352,553 B1 | 3/2002 | van der Burg et al. | |
| 6,352,561 B1 | 3/2002 | Leopold et al. | |
| 6,508,803 B1 | 1/2003 | Horikawa et al. | |
| 6,878,153 B2 | 4/2005 | Linder et al. | |
| 6,951,570 B2 | 10/2005 | Linder et al. | |
| 6,962,598 B2 | 11/2005 | Linder et al. | |
| 6,997,939 B2 | 2/2006 | Linder et al. | |
| 7,678,068 B2 | 3/2010 | Levine et al. | |
| 8,834,550 B2 | 9/2014 | Leanna et al. | |
| 8,870,806 B2 | 10/2014 | Levine et al. | |
| 8,961,582 B2 | 2/2015 | Holm et al. | |
| 9,084,669 B2 | 7/2015 | Meade et al. | |
| 9,155,609 B2 | 10/2015 | Levine et al. | |
| 9,237,944 B2 | 1/2016 | Meade et al. | |
| 9,278,020 B2 | 3/2016 | Levine et al. | |
| 9,402,755 B2 | 8/2016 | Norris et al. | |
| 9,526,648 B2 | 12/2016 | Sharma | |
| 9,579,186 B2 | 2/2017 | Hingston et al. | |
| 2002/0007208 A1 | 1/2002 | Strecker | |
| 2004/0064179 A1 | 4/2004 | Linder et al. | |
| 2005/0143773 A1 | 6/2005 | Abrams et al. | |
| 2010/0331960 A1 | 12/2010 | Clerc et al. | |
| 2013/0158646 A1* | 6/2013 | Roeder | A61F 2/966 623/1.11 |
| 2013/0211498 A1 | 8/2013 | Buckley et al. | |
| 2015/0081005 A1 | 3/2015 | Headley, Jr. et al. | |
| 2015/0282960 A1 | 10/2015 | Harris | |
| 2015/0374484 A1 | 12/2015 | Hingston et al. | |
| 2016/0081832 A1 | 3/2016 | Hingston et al. | |
| 2016/0317336 A1 | 11/2016 | Norris et al. | |

* cited by examiner

STENT AND SLEEVE DEPLOYMENT

CROSS-REFERENCE TO RELATED APPLICATIONS

This application claims priority to U.S. Provisional Application Ser. No. 62/521,129, filed Jun. 16, 2017, the entirety of which is incorporated herein by reference.

TECHNICAL FIELD

The present disclosure relates generally to methods and apparatuses for various digestive ailments. More particularly, the disclosure relates to different configurations and methods of manufacture and use of a stent.

BACKGROUND

Implantable stents are devices that are placed in a body structure, such as a blood vessel, esophagus, trachea, biliary tract, colon, intestine, stomach or body cavity, to provide support and to maintain the structure open. These devices are manufactured by any one of a variety of different manufacturing methods and may be used according to any one of a variety of methods. Of the known medical devices, delivery systems, and methods, each has certain advantages and disadvantages. There is an ongoing need to provide alternative medical devices and delivery devices as well as alternative methods for manufacturing and using medical devices and delivery devices.

SUMMARY

This disclosure is directed to several alternative designs, materials, and methods of manufacturing medical device structures and assemblies, for preventing leaks after an anastomosis surgery and/or treating various gastro-intestinal, digestive, or other ailments.

In a first example, a delivery system for delivering an implant to a body lumen may comprise an outer tubular member defining a lumen and having a proximal end region and a distal end region. An inner tubular member defining a lumen and having a proximal end region and a distal end region may be slidably disposed within the lumen of the outer tubular member. The inner tubular member may have at least one opening positioned in a side wall adjacent to the distal end region, the at least one opening extending from an outer surface to an inner surface of the inner tubular member. An expandable implant may be disposed about the outer surface of the inner tubular member adjacent the distal end region of the inner tubular member, the implant comprising at least a first rigid portion and a first flexible portion. A thread including a distal portion may be wrapped around the first flexible portion of the implant and may be configured to maintain the first flexible portion in a collapsed configuration. The distal end region of the outer tubular member may be disposed over the first rigid portion of the implant and may be configured to maintain the first rigid portion in a radially collapsed configuration.

Alternatively or additionally to any of the examples above, in another example, a distal end of the thread may be positioned adjacent to a proximal end region of the first flexible portion and the thread may be wrapped from the proximal end region to a distal end region of the first flexible portion.

Alternatively or additionally to any of the examples above, in another example, a distal end of the thread may be positioned adjacent to a distal end region of the first flexible portion and the thread may be wrapped from the distal end region to a proximal end region of the first flexible portion.

Alternatively or additionally to any of the examples above, in another example, a proximal portion of the thread may extend into the lumen of the inner tubular member through the at least one opening and extends proximally to a proximal end configured to remain outside the proximal end region of the inner tubular member.

Alternatively or additionally to any of the examples above, in another example, the system may further comprise a pulling member coupled to the proximal end of the thread.

Alternatively or additionally to any of the examples above, in another example, the distal portion of the thread wrapped around the first flexible portion of the implant may include a plurality of releasable knots.

Alternatively or additionally to any of the examples above, in another example, the first rigid portion may comprise a self-expanding stent.

Alternatively or additionally to any of the examples above, in another example, the first flexible portion may comprise a flexible membrane.

Alternatively or additionally to any of the examples above, in another example, the implant may further comprise a second rigid portion and a second flexible portion.

Alternatively or additionally to any of the examples above, in another example, the first flexible portion may be positioned between the first rigid portion and the second rigid portion and a proximal end region of the second flexible portion may be coupled to a distal end region of the second rigid portion.

Alternatively or additionally to any of the examples above, in another example, the at least one opening may comprise a first proximal opening, a second opening, a third opening, and a fourth distal opening, the second and third openings positioned between the first and fourth openings.

Alternatively or additionally to any of the examples above, in another example, the distal portion of the thread may be configured to be woven in and out of the first, second, third and/or fourth openings such that the distal portion of the thread is selectively wrapped around the first and second flexible portions.

Alternatively or additionally to any of the examples above, in another example, a distal end of the thread may be positioned adjacent to a proximal end region of the first flexible portion and the thread may be wrapped from the proximal end region to a distal end region of the first flexible portion, enter the lumen of the inner tubular member through the second opening, exit the lumen of the inner tubular member through the third opening, is wrapped from a proximal end region to a distal end region of the second flexible portion, and re-enters the lumen of the inner tubular member through the fourth opening.

Alternatively or additionally to any of the examples above, in another example, a distal end of the thread may be positioned adjacent to a distal end region of the second flexible portion and the thread may be wrapped from the distal end region to a proximal end region of the second flexible portion, enter the lumen of the inner tubular member through the third opening, exit the lumen of the inner tubular member through the second opening, is wrapped from a distal end region to a proximal end region of the first flexible portion, and re-enters the lumen of the inner tubular member through the first opening.

Alternatively or additionally to any of the examples above, in another example, the second rigid portion may comprise a stent and the second flexible portion may comprise a flexible membrane.

In another example, a delivery system for delivering an implant to a body lumen may comprise an outer tubular member defining a lumen and having a proximal end region and a distal end region and an inner tubular member defining a lumen and having a proximal end region and a distal end region. The inner tubular member may be slidably disposed within the lumen of the outer tubular member and have at least one opening positioned in a side wall adjacent to the distal end region. The at least one opening may extend from an outer surface to an inner surface of the inner tubular member. An expandable implant may be disposed about the outer surface of the inner tubular member adjacent the distal end region of the inner tubular member. The implant may comprise at least a first rigid portion and a first flexible portion. A thread including a distal portion may be wrapped around the first flexible portion of the implant and may be configured to maintain the first flexible portion in a collapsed configuration. The distal end region of the outer tubular member may be disposed over the first rigid portion of the implant and may be configured to maintain the first rigid portion in a radially collapsed configuration.

Alternatively or additionally to any of the examples above, in another example, a distal end of the thread may be positioned adjacent to a proximal end region of the first flexible portion and the thread may be wrapped from the proximal end region to a distal end region of the first flexible portion.

Alternatively or additionally to any of the examples above, in another example, a distal end of the thread may be positioned adjacent to a distal end region of the first flexible portion and the thread may be wrapped from the distal end region to a proximal end region of the first flexible portion.

Alternatively or additionally to any of the examples above, in another example, a proximal portion of the thread may extend into the lumen of the inner tubular member through the at least one opening and extends proximally to a proximal end configured to remain outside the proximal end region of the inner tubular member.

Alternatively or additionally to any of the examples above, in another example, the system may further comprise a pulling member coupled to the proximal end of the thread.

Alternatively or additionally to any of the examples above, in another example, the distal portion of the thread wrapped around the first flexible portion of the implant may include a plurality of releasable knots.

Alternatively or additionally to any of the examples above, in another example, the first rigid portion may comprise a self-expanding stent.

Alternatively or additionally to any of the examples above, in another example, the first flexible portion may comprise a flexible membrane.

In another example, a delivery system for delivering an implant to a body lumen may comprise an outer tubular member defining a lumen and having a proximal end region and a distal end region and an inner tubular member defining a lumen and having a proximal end region and a distal end region. The inner tubular member may be slidably disposed within the lumen of the outer tubular member and may have a first proximal opening, a second opening distal to the first opening, a third opening distal to the second opening, and a fourth opening distal to the third opening, the first, second, third, and fourth openings positioned in a side wall adjacent to the distal end region and extending from an outer surface to an inner surface of the inner tubular member. An expandable implant may be disposed about the outer surface of the inner tubular member adjacent the distal end region of the inner tubular member. The implant may comprise a first rigid portion, a first flexible portion, a second rigid portion, and a second flexible portion. A thread including a distal portion may be wrapped around the first flexible portion and the second flexible portion of the implant and may be configured to maintain the first and second flexible portions in a radially collapsed configuration. The distal end region of the outer tubular member may be disposed over the first rigid portion and the second rigid portion of the implant and may be configured to maintain the first and second rigid portions in a radially collapsed configuration.

Alternatively or additionally to any of the examples above, in another example, the first flexible portion may be positioned between the first rigid portion and the second rigid portion and a proximal end region of the second flexible portion may be coupled to a distal end region of the second rigid portion.

Alternatively or additionally to any of the examples above, in another example, the distal portion of the thread may be configured to be woven in and out of the first, second, third and/or fourth openings such that the distal portion of thread is selectively wrapped around the first and second flexible portions.

Alternatively or additionally to any of the examples above, in another example, a distal end of the thread may be positioned adjacent to a proximal end region of the first flexible portion and the thread may be wrapped from the proximal end region to a distal end region of the first flexible portion, enters the lumen of the inner tubular member through the second opening, exits the lumen of the inner tubular member through the third opening, is wrapped from a proximal end region to a distal end region of the second flexible portion, and re-enters the lumen of the inner tubular member through the fourth opening.

Alternatively or additionally to any of the examples above, in another example, a distal end of the thread may be positioned adjacent to a distal end region of the second flexible portion and the thread may be wrapped from the distal end region to a proximal end region of the second flexible portion, enters the lumen of the inner tubular member through the third opening, exits the lumen of the inner tubular member through the second opening, is wrapped from a distal end region to a proximal end region of the first flexible portion, and re-enters the lumen of the inner tubular member through the first opening.

Alternatively or additionally to any of the examples above, in another example, a proximal portion of the thread may extend into the lumen of the inner tubular member through at least one of the first, second, third, or fourth openings and may extend proximally to a proximal end configured to remain outside the proximal end region of the inner tubular member.

Alternatively or additionally to any of the examples above, in another example, the system may further comprise a pulling member coupled to the proximal end of the thread.

Alternatively or additionally to any of the examples above, in another example, the distal portion of the thread may be wrapped around the first and/or second flexible portions of the implant includes a plurality of releasable knots.

In another example, a method for delivering an implant to a body lumen may comprise advancing a delivery system to a target location in a body lumen. The delivery system may comprise an outer tubular member defining a lumen and having a proximal end region and a distal end region, an inner tubular member defining a lumen and having a proximal end region and a distal end region, the inner tubular member may be slidably disposed within the lumen of the outer tubular member and have at least one opening positioned in a side wall adjacent to the distal end region, the at least one opening may extend from an outer surface to an inner surface of the inner tubular member, an expandable implant may be disposed about the outer surface of the inner tubular member adjacent the distal end region of the inner tubular member, the implant may comprise at least a first rigid portion and a first flexible portion, and a thread including a distal portion wrapped around the first flexible portion of the implant and configured to maintain the first flexible portion in a collapsed configuration. The distal end region of the outer tubular member may be disposed over the first rigid portion of the implant and is configured to maintain the first rigid portion in a radially collapsed configuration. The method may further comprise applying a pulling force to a proximal portion of the thread to unravel the thread wrapped around the first flexible portion and proximally retracting the outer tubular member relative to the inner tubular member to deploy the first rigid portion of the expandable implant from the outer tubular member.

Alternatively or additionally to any of the examples above, in another example, the distal portion of the thread may be wrapped about the first flexible portion such that the first flexible portion expands from the collapsed configuration to an expanded configuration in a distal to proximal direction as the thread is unraveled.

Alternatively or additionally to any of the examples above, in another example, the distal portion of the thread may be wrapped about the first flexible portion such that the first flexible portion expands from the collapsed configuration to an expanded configuration in a proximal to distal direction as the thread is unraveled.

Alternatively or additionally to any of the examples above, in another example, the first rigid portion may comprise a self-expanding stent.

Alternatively or additionally to any of the examples above, in another example, upon proximally retracting the outer tubular member the first rigid portion may expand from the radially collapsed configuration to a radially expanded configuration.

The above summary of exemplary embodiments is not intended to describe each disclosed embodiment or every implementation of the present disclosure.

BRIEF DESCRIPTION OF THE DRAWINGS

The invention may be more completely understood in consideration of the following detailed description of various embodiments in connection with the accompanying drawings, in which.

Figure 1:
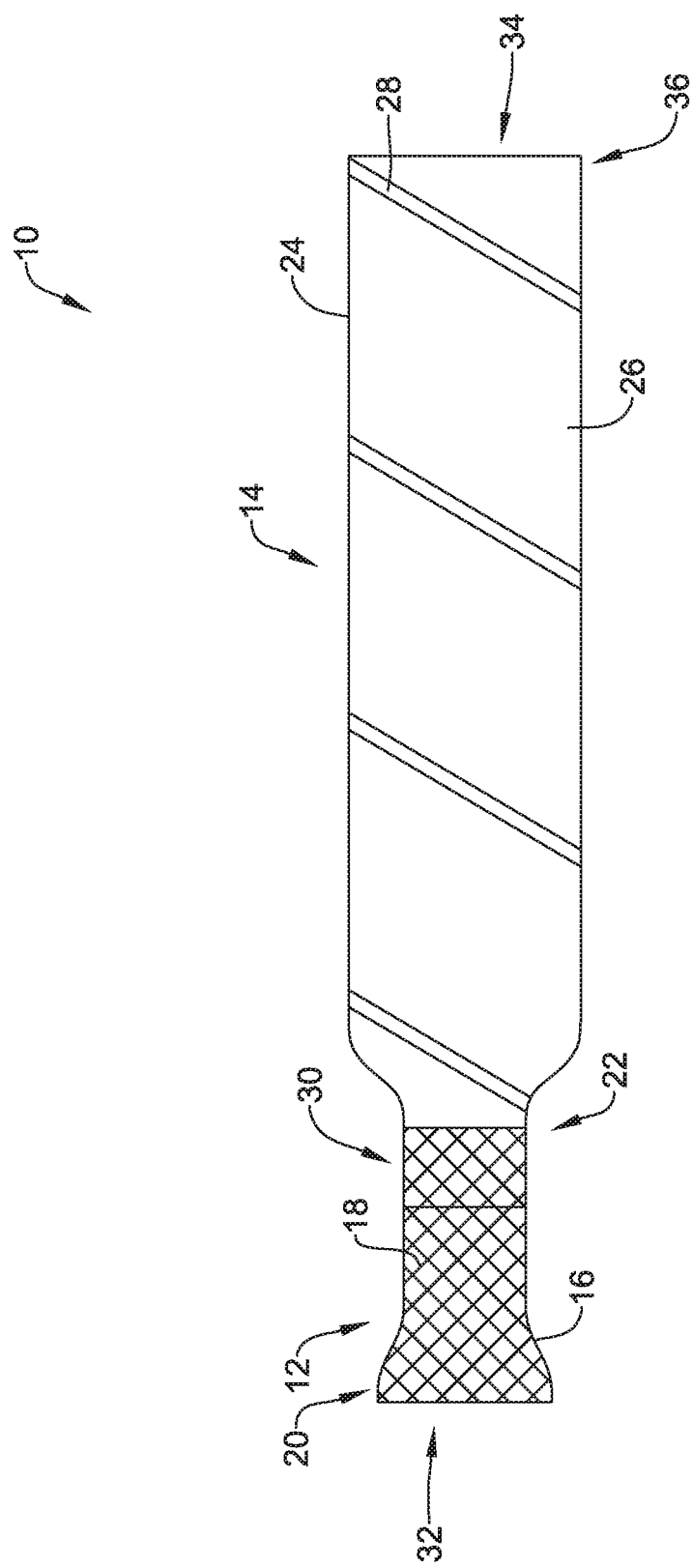
FIG. 1 is a side view of an illustrative implant including a flexible sleeve.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may be indicative as including numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

Although some suitable dimensions, ranges, and/or values pertaining to various components, features and/or specifications are disclosed, one of the skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

For purposes of this disclosure, "proximal" refers to the end closer to the device operator during use, and "distal" refers to the end further from the device operator during use.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

It is noted that references in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with one embodiment, it should be understood that such feature, structure, or characteristic may also be used connection with other embodiments whether or not explicitly described unless cleared stated to the contrary.

As self-expanding stent systems evolve, their usage with attached polymeric sleeves may be considered for numerous applications such as, but not limited to, the treatment of gastroesophageal reflux disease (GERD), obesity and/or diabetes treatments (e.g., to reduce the absorption of nutrients), and/or to protect against post bariatric surgery leaks or other damage. In other examples, sleeves may be deployed in a patient's colon to protect a damaged area. In a variety of contexts, sleeves may be made of a material that lacks rigidity and support, making them difficult to deploy within the desired body lumen.

For example, the sleeve material may kink or bunch during attempted deployment. Alternative delivery systems, which may include various deployment options, are desired to accommodate delivery of a more rigid stent structure and a more flexible sleeve structure.

FIG. 1 illustrates a side view of an illustrative implant 10 including a first portion 12 and a second portion 14. In some cases, the first portion 12 may take the form of a stent 16 including an elongated tubular stent frame 18. The stent 16 may be may be entirely, substantially or partially, covered with a polymeric covering, such as a coating (not explicitly shown). The covering may be disposed on an inner surface and/or outer surface of the stent 16, as desired. When so provided a polymeric covering may reduce or eliminate tissue ingrowth and/or reduce food impaction. The stent 16 may include regions of differing diameters. For example, the stent 16 may include a flared (e.g., enlarged relative to other portions of the stent 16) proximal end region 20. While not explicitly shown, the distal end region 22 of the stent 16 may also include a flared end region. The stent frame 18 may be expandable between a radially collapsed delivery configuration and a radially expanded deployed configuration. The expanded configuration may secure the implant 10 at the desired location in a body lumen. In some cases, the implant 10 may include features (e.g., anti-migration flares, fixation spikes, sutures, etc.) to prevent distal/proximal displacement and/or migration of the implant 10, once the implant 10 is positioned and expanded in the body lumen.

The stent frame 18 may have a woven structure, fabricated from a number of filaments. In some embodiments, the stent frame 18 may be braided with one filament. In other embodiments, the stent frame 18 may be braided with several filaments, as is found, for example, in the WallFlex®, WALLSTENT®, and Polyflex® stents, made and distributed by Boston Scientific. In another embodiment, the stent frame 18 may be knitted, such as the Ultraflex™ stents made by Boston Scientific. In yet another embodiment, the stent frame 18 may be of a knotted type, such the Precision Colonic™ stents made by Boston Scientific Scimed, Inc. In still another embodiment, the stent frame 18 may be laser cut, such as the EPIC™ stents made by Boston Scientific.

It is contemplated that the stent frame 18 can be made from a number of different materials such as, but not limited to, metals, metal alloys, shape memory alloys and/or polymers, as desired, enabling the stent 16 to be expanded into shape when accurately positioned within the body. In some instances, the material may be selected to enable the stent 16 to be removed with relative ease as well. For example, the stent frame 18 can be formed from alloys such as, but not limited to, nitinol and Elgiloy®. Depending the on material selected for construction, the stent 16 may be self-expanding (i.e., configured to automatically radially expand when unconstrained). In some embodiments, fibers may be used to make the stent frame 18, which may be composite fibers, for example, having an outer shell made of nitinol having a platinum core. It is further contemplated the stent frame 18 may be formed from polymers including, but not limited to, polyethylene terephthalate (PET). In some embodiments, the stent 16 may be self-expanding while in other embodiments, the stent 16 may be expand by an expansion device (such as, but not limited to a balloon inserted within the lumen 32 of the stent 16). As used herein the term "self-expanding" refers to the tendency of the stent to return to a preprogrammed diameter when unrestrained from an external biasing force (for example, but not limited to a delivery catheter or sheath). The stent 16 may include a one-way valve, such as an elastomeric slit valve or duck bill valve, positioned within the lumen 32 thereof to prevent retrograde flow of gastrointestinal fluids.

In some cases, the second portion 14 may take the form of a flexible sleeve 24. The sleeve 24 may include a membrane 26 and a support 28. A lumen 34 may extend the length of the sleeve 24 and be in fluid communication with the lumen 32 of the stent 16. The sleeve 24 may be connected, affixed, or secured to the distal end region 22 of the stent 16 adjacent to a proximal end region 30 of the sleeve 24. In some cases, the sleeve 24 may extend into a lumen 32 of the stent 16, as shown in FIG. 1, although this is not required. In other embodiments, the sleeve 24 may extend partially, substantially, or all of a length of the implant 10 and cover all other portions (exterior surface and/or interior surface) of the implant 10, including the stent 16. The membrane 26 may couple the sleeve 24 to the stent 16. In some cases, the membrane 26 may be secured by an adhesive or other methods known in the art, including by not limited to thermal methods, mechanical methods, etc.

The sleeve 24 may extend from the distal end region 22 of the stent 16 and may have an elongated, tubular shape with an interior lumen 34. In one example, the membrane 26 defines only one interior lumen. However, other embodiments including more than one lumen are contemplated. In an expanded configuration, the sleeve 24 may be substantially cylindrical. Absent the support 28, the membrane 26 may be a flexible, thin membrane that readily collapses on itself. However the support 28 may provide rigidity and structure to sleeve 24. Some examples and discussion of illustrative supports 28 may be found in Patent Application No. 62/419,707, filed on Nov. 9, 2016, titled DEPLOYABLE SLEEVES AND RELATED METHODS, the disclosure of which is incorporated herein by reference. Generally, the support 28 may be a helically wound element configured to assume an expanded configuration either upon the release of a biasing force or upon application of a force thereto. In various examples, the support 28 may include different materials that provide different levels of rigidity. Rigidity may be varied through material selection, pitch, etc. It is further contemplated that the rigidity may vary along the length of the sleeve 24, as desired. The support 28 may extend along a perimeter of the sleeve 24. The support 28 may be positioned between two or more layers of material that form the membrane 26 (e.g., an interior layer and an exterior layer), or otherwise embedded into the material that forms the membrane 26. In other examples, support 28 may extend along the perimeter of sleeve 24 by being positioned proximate to the membrane 26, either interior to or exterior to the membrane 26.

The membrane 26 may include one or more of the following polymer materials: polyethylene, polypropylene, polystyrene, polyester, biosorbable plastics (e.g., polylactic acid), polycarbonate, polyvinyl chloride, polyacrylate, acrylate, polysulfone, polyetheretherketone, thermoplastic elastomers, thermoset elastomers (e.g., silicone), poly-p-xylylene (parylene), flouropolymers (e.g., polytetrafluoroethylene (PTFE), polyvinylidene fluoride (PVDF), poly(vinylidene fluoride-co-hexafluoropropylene) (PVDFHFP)), bioplastics (e.g., cellulose acetate). The sleeve may additionally or alternatively include one or more of: polyurethane and its copolymers, ethylene vinyl-acetate, polyethylene terephthalate (PET), polyolefins, cellulosics, polyamides, acrylonitrile butadiene styrene copolymers, styrene isoprene butadiene (SIBS) block copolymers, acrylics, poly(glycolide-lactide) copolymer, Tecothane, PEBAX, poly(γ-caprolactone), poly(γ-hydroxybutyrate), polydioxanone, poly(γ-ethyl glutamate), polyiminocarbonates, poly(ortho ester), and/or polyanhydrides. Blends of the above polymers may also be employed.

In further detail, the implant 10 may be generally cylindrical in shape, although this is not required, substantially flexible, and sized appropriately for a convenient accommodation within the digestive tract. It is contemplated that various shapes, sizes and designs of the implant may be constructed depending on the size and geometry of the cavities where the implant 10 has to be placed. In various examples, the implant may have a length between 3-12 inches, 3-6 inches, 0.5-20 feet (0.15-6.1 meters), between 3-5 feet (0.9-1.5 meters), or about 2-4 feet (0.6-1.2 meters). However, the implant 10 may have a length of less than 0.5 feet (0.15 meters) or greater than 20 feet (6.1 meters).

Once implanted in a patient, the stent 16 may exert a radially outward force to help secure the implant 10 to the body lumen. The implant 10 may be positioned in the esophagus, the gastro-esophageal junction (GEJ) region, or at or near the pylorus with the sleeve 24 extending through the stomach or other portions of the gastro-intestinal system. In another example, the stent 16 may be positioned in the patient's intestine. In some examples, the implant 10 does not include the stent 16. Instead, the sleeve 24 may be secured directly to the patient's tissue using sutures or any other suitable attachment mechanism.

Figure 2:
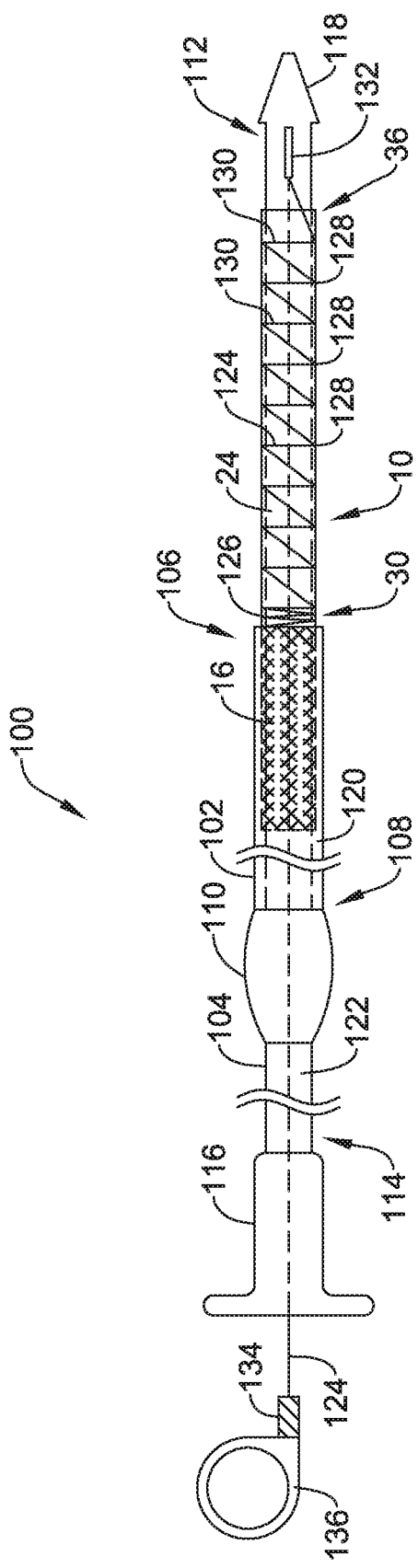
FIG. 2 is a side view of an illustrative delivery system for delivering the implant of FIG. 1.

FIG. 2 is a side view of an illustrative delivery system 100 for delivering an implant having both a rigid portion and a flexible portion, such as the implant 10 described herein, to a target region. The delivery system 100 may include an outer or exterior elongate shaft or tubular member 102 and an inner elongate shaft or tubular member 104. The inner tubular member 104 may be slidably disposed within a lumen of the outer tubular member 102. The outer tubular member 102 may extend proximally from a distal end region 106 to a proximal end region 108 configured to remain outside of a patient's body. A first hub or handle 110 may be coupled to the proximal end region 108 of the outer tubular member 102. The inner tubular member 104 may extend proximally from a distal end region 112 to a proximal end region 114 configured to remain outside of a patient's body. A second hub or handle 116 may be coupled to the proximal end region 114 of the inner tubular member 104. The inner tubular member 104 may further include a distal tip 118 positioned adjacent to the distal end region 112. The distal tip 118 may be configured to be atraumatic.

The outer tubular member 102 may include a lumen 120 extending from the distal end region 106 to the proximal end region 108. The lumen 120 may also extend through the first handle 110. The lumen 120 of the outer shaft 102 and the first handle 110 may be configured to slidably receive the inner shaft 104. The inner tubular member 104 may include a lumen 122 extending from the distal end region 112 to the proximal end region 114. The lumen 122 of the inner tubular shaft 104 may also extend through the second handle 116. The lumen 122 of the inner shaft 104 may be configured to receive a thread, pull-wire and/or guidewire, as desired.

The implant 10 may be disposed around a portion of the inner tubular member 104 at or adjacent to the distal end region 112 thereof. When the implant 10 is disposed over the inner tubular member 104, in a delivery configuration, the stent portion 16 may be restrained in a collapsed reduced diameter or delivery configuration by the outer tubular member 102 surrounding the stent portion 16. The distal end region 106 of the outer tubular member 102 may be positioned such that the outer tubular member 102 surrounds and covers the length of stent 16 during delivery. The outer tubular member 102 may have sufficient hoop strength to retain the stent 16 in its reduced diameter state.

The sleeve 24 may be held in a radially collapsed configuration through the use of a thread 124 (e.g., filament or wire). The thread 124 may be any thin flexible element capable of being wrapped and unwrapped about the sleeve 24. A distal portion of the thread 124 may be wound or wrapped about the sleeve 24 while a proximal portion of the thread 124 may extend proximally through the lumen 122 to a point outside the delivery device 100. The thread 124 may be wound about an outer surface of the sleeve 24 to apply a biasing force to the sleeve 24 which maintains the sleeve 24 in a collapsed or reduced diameter configuration. In some embodiments, a distal end 126 of the thread 124 may be positioned adjacent to the proximal end region 30 of the sleeve 24. In other embodiments, the distal end 126 of the thread 124 may be positioned adjacent to the distal end region 36 of the sleeve 24 as described in more detail with respect to FIGS. 8 and 9. It is contemplated that the position of the distal end 126 of the thread 124 may determine which portion of the sleeve 24 (e.g., proximal or distal) is expanded first. In some cases, the thread 124 may be wound such that the clinician may have the option of selecting which portion of the sleeve 24 is deployed first.

The thread 124 may be wrapped around the sleeve 24 in a generally helical manner, although this is not required. The spacing of adjacent windings 130 of the thread 124 may be uniform or variable as desired. In other words the pitch of the windings 130 may be the same, varied, or combinations thereof, as desired. In some cases, the thread 124 may include a plurality of knots 128 similar in form and function to those used in knitting or crocheting, which allow the thread 124 to be releasably secured about the sleeve 24. The knots 128 may generally maintain the thread 124 in a desired configuration while still allowing the thread 124 to be unraveled or removed as desired. In some cases, the thread 124 may not include knots 128.

The thread 124 may extend through a skive, slot, or other opening 132 in a side wall of the inner tubular member 104 and into the lumen 122 of the inner tubular member 104. The opening 132 may extend from an outer surface to an inner surface of the inner tubular member 104 to allow the thread 124 (or other components, as desired) to extend between the exterior of the inner tubular member 104 and the interior thereof. The thread 124 may extend proximally through the lumen 122 and exit proximally at the second handle 116. The proximal end 134 of the thread 124 is configured to remain outside of the inner tubular member 104 and may be coupled to or otherwise affixed to a pull member 136 or other actuation mechanism. The pull member 136, such as a pull ring, a pull tab, or the like, may facilitate actuation of thread 124; however a pull member 136 or other actuation mechanism may not be present or required.

Figure 3:
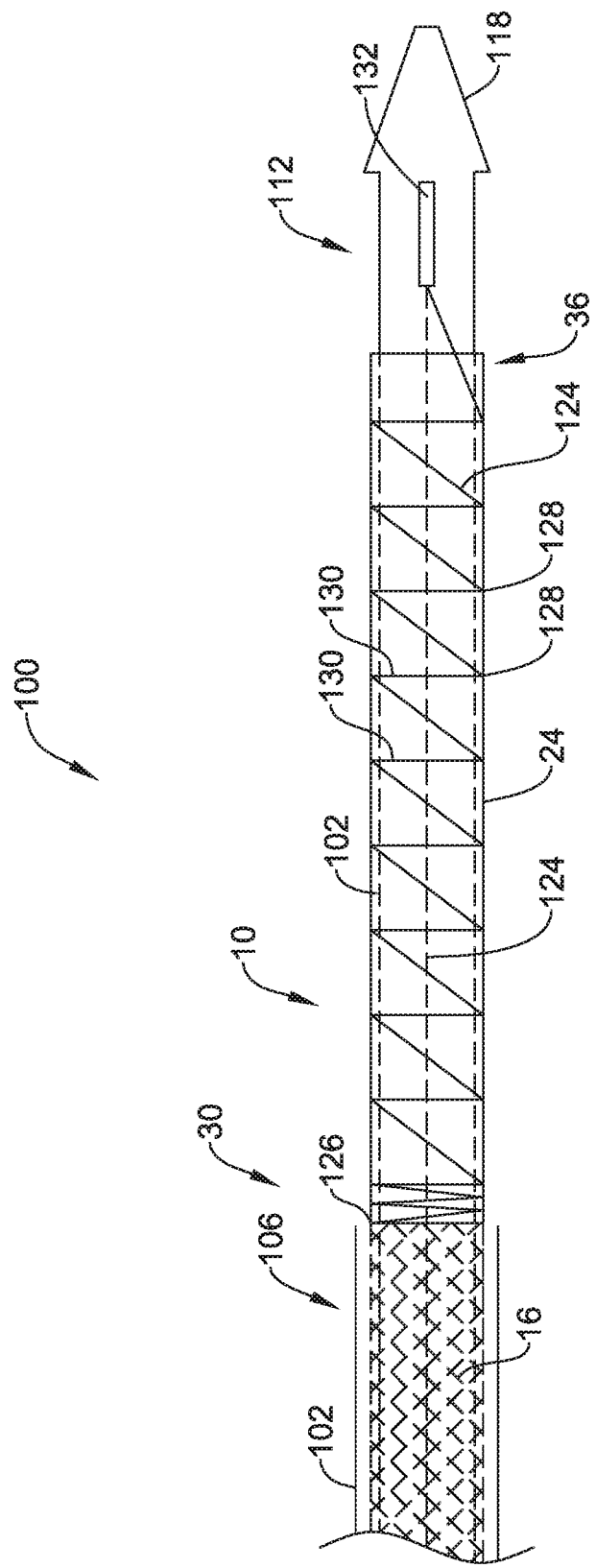
FIGS. 3-7 illustrate a method for delivering the illustrative implant of FIG. 1.

FIGS. 3-7 illustrate a method of delivering the illustrative implant 10 to a body lumen using the delivery device 100 of FIG. 2. FIG. 3 illustrates a close up side view of a distal portion of the delivery device 100 with the implant 10 in a collapsed or delivery configuration. The delivery device 100 may be advanced through the gastrointestinal tract transorally or transrectally, as desired. The delivery device 100 may be advanced with or without the use of a guidewire. Once the implant 10 is positioned adjacent to the target region, the restraining forces maintaining the stent 16 and the sleeve 24 in the radially collapsed configuration may be removed either in series (one after the other) or simultaneously (e.g., together) to deploy the implant 10.

Figure 4:
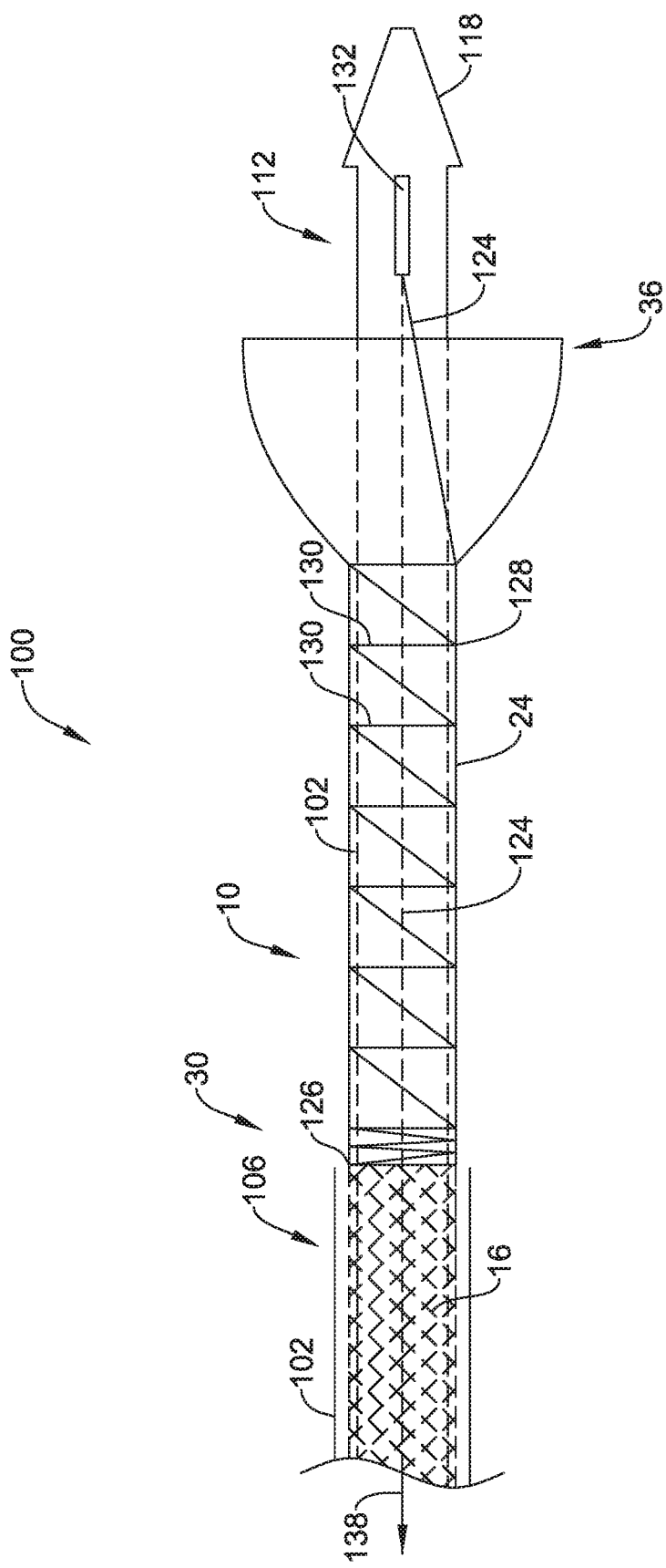
Figure 5:
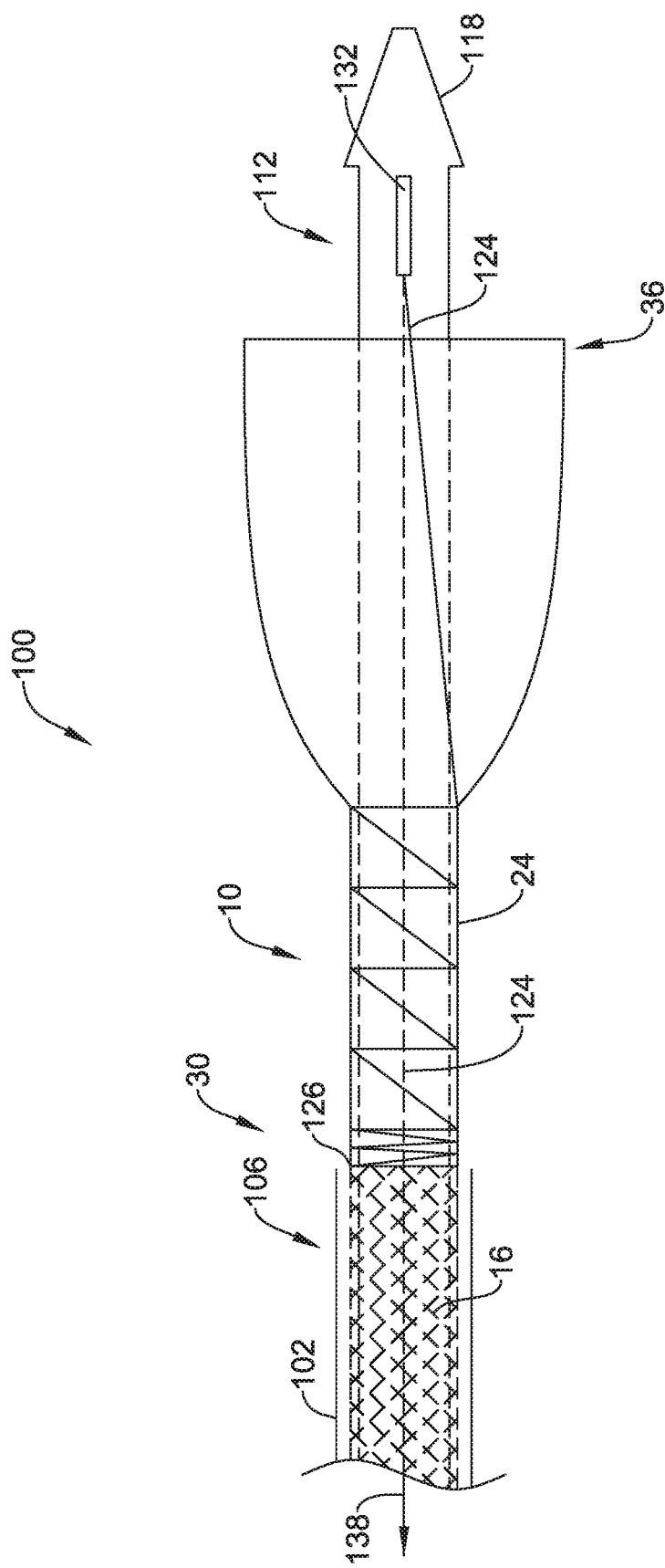
Figure 6:
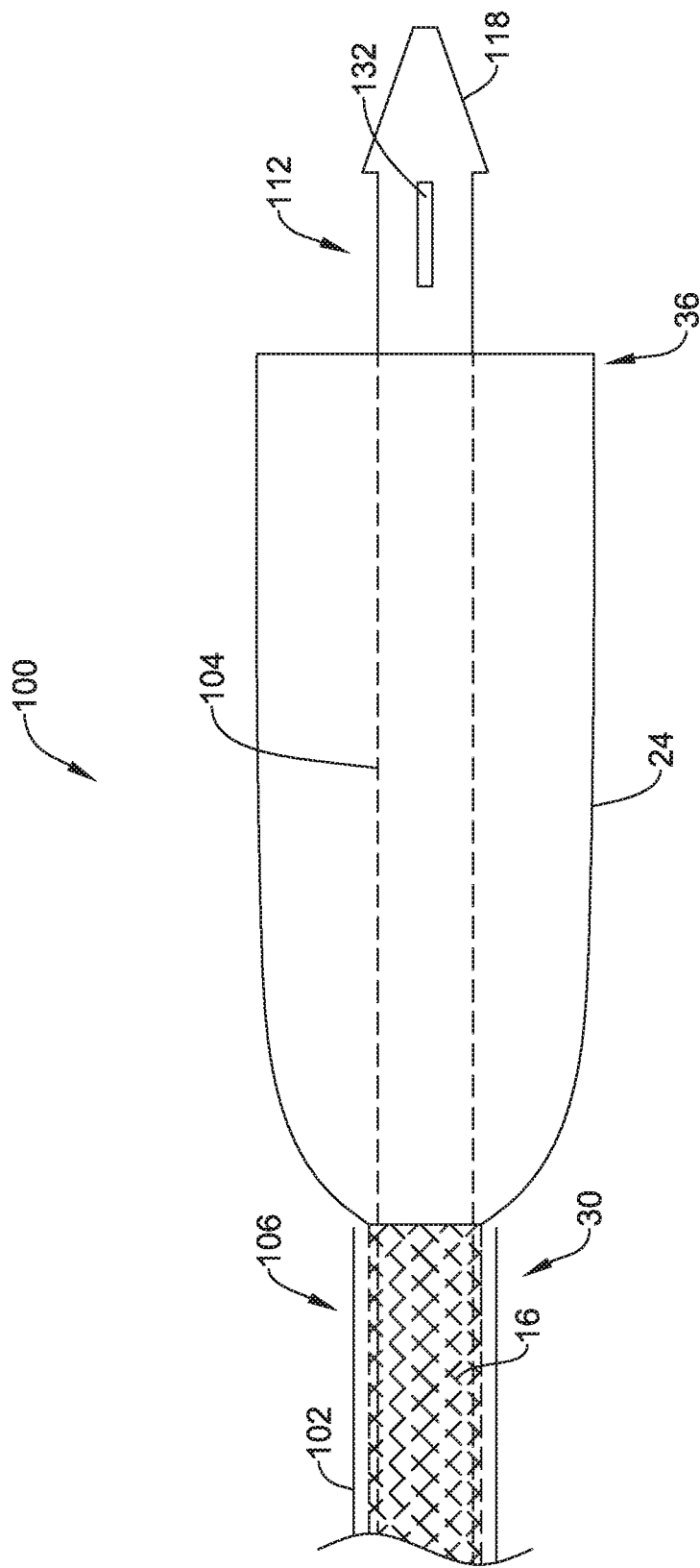

In some cases, the sleeve 24 may be deployed prior to the stent 16. Once the implant 10 is adjacent to the desired location, a proximal or pulling force 138 may be applied to the proximal end 134 of the thread 124, as shown in FIG. 4. In some cases, the pulling force 138 may be applied by placing a finger inside of the pull member 136 and pulling away from the handle 116. As the member 136 is pulled or actuated, the thread 124 begins to unravel. In the embodiments shown in FIGS. 2-7, the thread 124 is wrapped or wound such that the thread 124 disposed over the distal portion 36 of the sleeve 24 is removed or unraveled first. Still referring to FIG. 4, as the biasing force of the thread 124 is released as the thread 124 is unraveled, the sleeve 24 begins to radially expand into its unbiased or deployed configuration. As the thread 124 is pulled, the portion of the thread 124 previously wound around the sleeve 24 unravels and enters the lumen 122 through the opening 132. The thread 124 then moves proximally through the lumen 122. Continued unraveling of the thread 124 will cause more of the length of the sleeve 24 to be released, as shown in FIG. 5. Proximal actuation of the proximal end 134 of the thread 124 may continue until the distal end 126 of the thread 124 has been completely unraveled, as shown in FIG. 6. It is contemplated that the clinician may continue to pull the thread 124 until the distal end 126 has been completely removed from the lumen 122 and the device 100 although this is not required.

Figure 7:
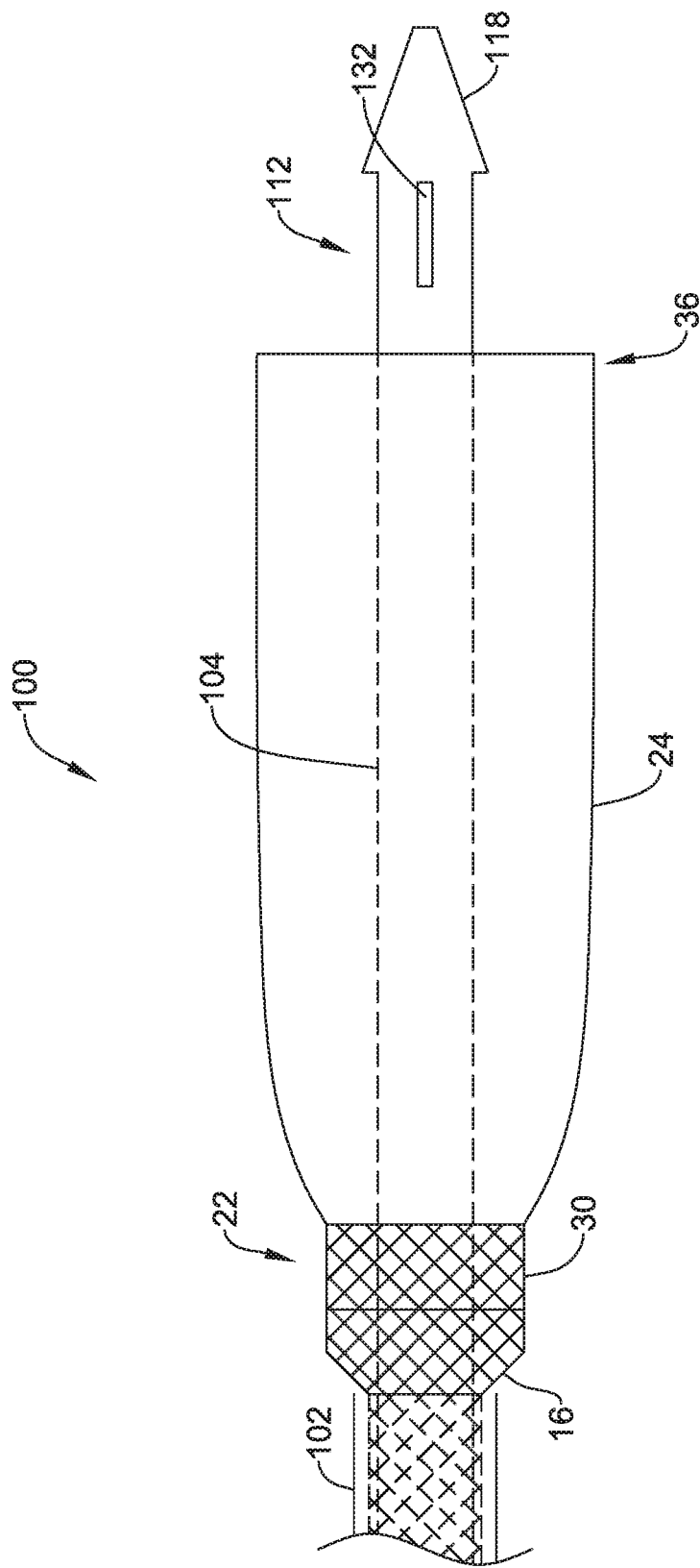

Once the sleeve 24 has been partially or fully deployed, the stent 16 may be released. It should be noted that it is not necessarily required to deploy the sleeve 24 first. In some cases, it may be desirable to deploy the stent 16 portion first, followed by deployment of the sleeve 24 by unraveling the thread 124 as discussed above. The stent 16 may be released by actuating the first handle 110 proximally relative to the second handle 116, e.g., by pulling the first handle 110 (see, for example, FIG. 2) proximally while maintaining the second handle 116 in a fixed position. Thus, the outer tubular shaft 102 may be retracted proximally relative to the inner tubular shaft 104. In other words, the outer tubular shaft 102 may be proximally retracted while the inner tubular shaft 104 is held stationary. As shown in FIG. 7, as the outer tubular shaft 102 is retracted proximally to uncover the stent 16, the biasing force is removed from the exterior of the stent 16 and the stent 16 assumes its radially expanded, unbiased, deployed configuration. Once the outer tubular member 102 no longer covers the proximal end 20 of the stent 16, the implant 10 may assume its fully deployed configuration, as shown in FIG. 1. The delivery device 100 may then be removed from the body lumen.

Figure 8:
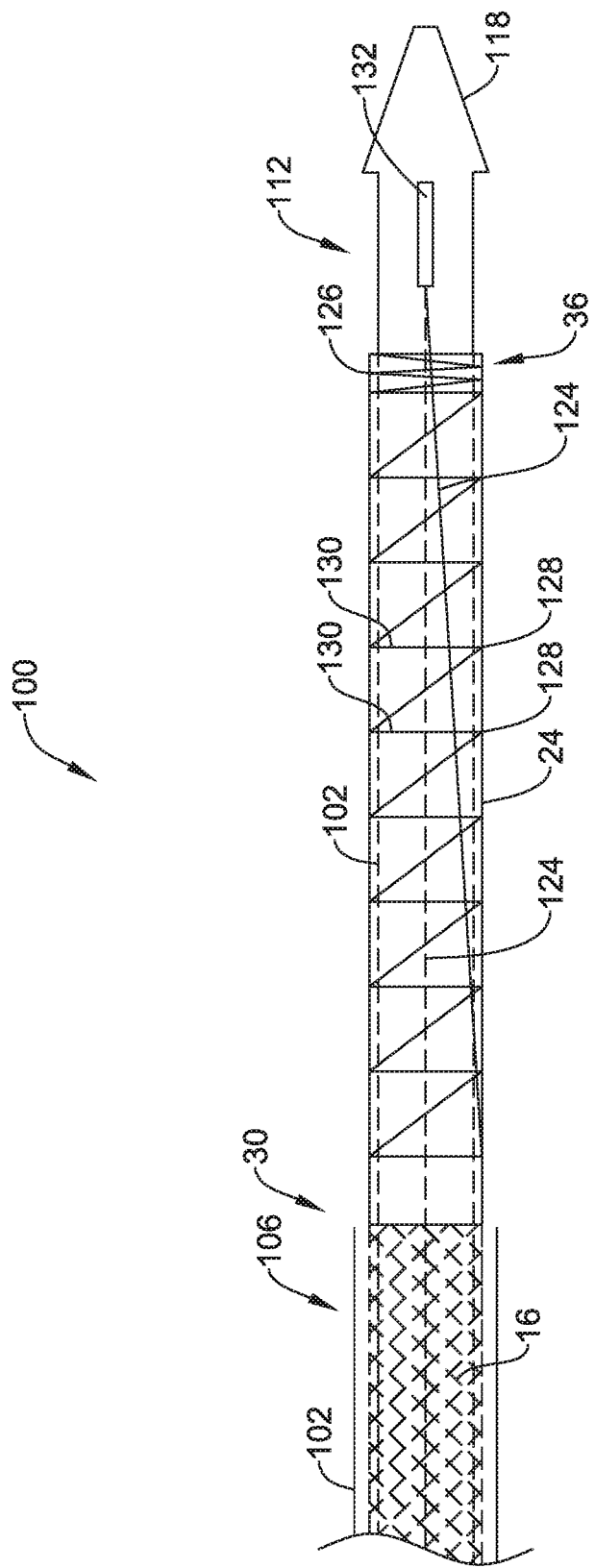
FIGS. 8-9 illustrate another illustrative method for delivering the illustrative implant of FIG. 1.
Figure 9:
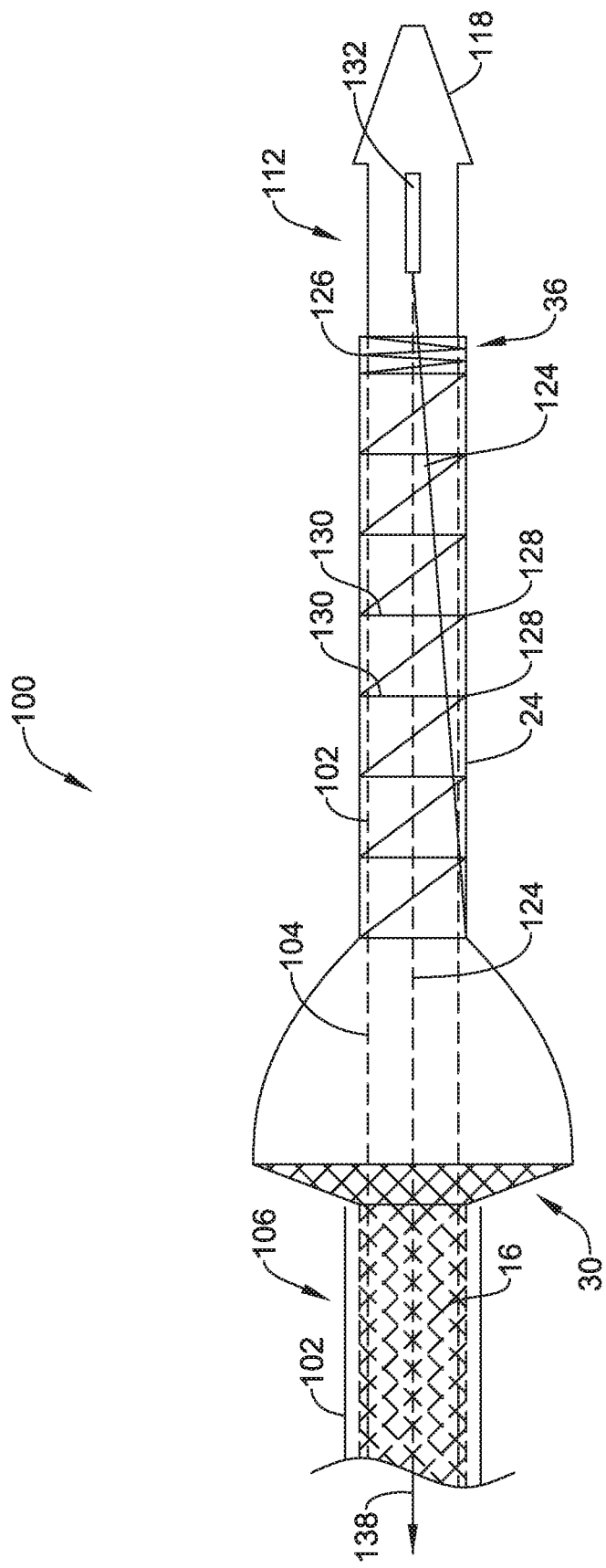

FIGS. 8-9 illustrate another method of delivering the implant 10 to a body lumen. The structure of the delivery device 100 may be substantially the same as described above with respect to FIG. 2. However, the thread 124 may be wound in a different direction such that the sleeve 24 is deployed proximally to distally (as opposed to distally to proximally, as shown in FIGS. 3-7).

FIG. 8 illustrates a close up side view of a distal portion of the delivery device 100 with the implant 10 in a radially collapsed or delivery configuration. The implant 10 may be disposed around a portion of the inner tubular member 104 at or adjacent to the distal end region 112 thereof. When the implant 10 is disposed over the inner tubular member 104, in a delivery configuration, the stent portion 16 may be restrained in a collapsed reduced diameter or delivery configuration by the outer tubular member 102 surrounding the stent portion 16. The distal end region 106 of the outer tubular member 102 may be positioned such that the outer tubular member 102 surrounds and covers the length of stent 16 during delivery. The outer tubular member 102 may have sufficient hoop strength to retain the stent 16 in its reduced diameter state.

The sleeve 24 may be held in a radially collapsed configuration through the use of a thread 124 (e.g., filament or wire). The thread 124 may be wound about an outer surface of the sleeve 24 to apply a biasing force to the sleeve which maintains it in a collapsed or reduced diameter configuration. In some embodiments, a distal end 126 of the thread 124 may be positioned adjacent to the distal end region 36 of the sleeve 24. The thread 124 may be wrapped around the sleeve 24 in a generally helical manner, although this is not required. The spacing of adjacent windings 130 of the thread 124 may be uniform or variable as desired. In other words the pitch of the windings 130 may be the same, varied, or combinations thereof, as desired. In some cases, the thread 124 may include a plurality of knots 128 similar in form and function to those used in knitting or crocheting, which allow the thread 124 to be releasably secured about the sleeve 24. The knots 128 may generally maintain the thread 124 in a desired configuration while still allowing the thread 124 to be unraveled or removed as desired. In some cases, the thread 124 may not include knots 128.

The thread 124 may extend through an opening 132 and into the lumen 122 of the inner tubular member 104. The opening 132 may extend from an outer surface to an inner surface of the inner tubular member 104 to allow the thread (or other components, as desired) to extend between the exterior of the inner tubular member 104 and the interior thereof. The thread 124 may extend proximally through the lumen 122 and exit proximally at the second handle 116. The proximal end 134 of the thread 124 may be coupled to or otherwise affixed to a pull member 136 or other actuation mechanism. The pull member 136, such as a pull ring, a pull tab, or the like, may facilitate actuation of thread 124; however a pull member 136 or other actuation mechanism may not be present or required.

The delivery device 100 may be advanced through the gastrointestinal tract transorally or transrectally, as desired. The delivery device 100 may be advanced with or without the use of a guidewire. Once the implant 10 is positioned adjacent to the target region, the restraining forces maintaining the stent 16 and the sleeve 24 in the radially collapsed configuration may be removed either in series (one after the other) or simultaneously (e.g., together) to deploy the implant 10.

In some cases, the stent 16 may be deployed prior to the sleeve 24. Once the implant is positioned adjacent to the desired location, the stent 16 may be released. The stent 16 may be released by actuating the first handle 110 proximally relative to the second handle 116, e.g., by pulling the first handle 110 (see, for example, FIG. 2) proximally while maintaining the second handle 116 in a fixed position. Thus, the outer tubular shaft 102 may be retracted proximally relative to the inner tubular shaft 104. In other words, the outer tubular shaft 102 may be proximally retracted while the inner tubular shaft 104 is held stationary. As shown in FIG. 9, as the outer tubular shaft 102 is retracted proximally to uncover the stent 16, the biasing force is removed from the exterior of the stent 16 and the stent 16 assumes its radially expanded, unbiased, deployed configuration. While FIG. 9 illustrates the stent 16 in a partially deployed configuration, the stent 16 may be fully deployed prior to deploying the sleeve 24.

Still referring to FIG. 9, once the stent 16 has been partially or fully deployed, deployment of the sleeve 24 may begin. A proximal or pulling force 138 may be applied to the proximal end 134 of the thread 124. In some cases, the pulling force 138 may be applied by placing a finger inside of the pull member 136 and pulling away from the handle 116. As the member 136 is pulled or actuated, the thread 124 begins to unravel. In the embodiments shown in FIGS. 8-9, the thread 124 is wrapped or wound such that the thread 124 disposed over the proximal portion 30 of the sleeve 24 is removed or unraveled first. As the biasing force of the thread 124 is released as the thread 124 is unraveled, the sleeve 24 begins to radially expand into its unbiased or deployed configuration. As the thread 124 is pulled, the portion of the thread 124 previously wound around the sleeve 24 unravels and enters the lumen 122 through the opening 132. The thread 124 then moves proximally through the lumen 122. Continued unraveling of the thread 124 will cause more of the length of the sleeve 24 to be released. Proximal actuation of the proximal end 134 of the thread 124 may continue until the distal end 126 of the thread 124 has been completely unraveled. It is contemplated that the clinician may continue to pull the thread 124 until the distal end 126 has been completely removed from the lumen 122 and the device 100 although this is not required. Once the outer tubular member 102 no longer covers the proximal end 20 of the stent 16 and the thread 124 has been removed, the implant 10 may assume its fully deployed configuration, as shown in FIG. 1. The delivery device 100 may then be removed from the body lumen.

While the opening 132 is illustrated as distal to the sleeve 24, it is contemplated that the opening 132 may be positioned in other locations as desired. In one example, the opening 132 in the inner tubular member 104 may be positioned adjacent to the stent 16. In other words, the opening 132 may be positioned underneath the stent 16 when the implant 10 is radially collapsed around the inner tubular member 104 in the delivery configuration. It is contemplated that the thread 124 may be threaded through the stent frame 18 and over the sleeve 24. In another example, the opening 132 may be placed in a sliding arrangement to allow for the opening of a knot, such as knot 128, at a proximal or a distal point on the sleeve 24. Such an arrangement may allow for a decision on release direction of the sleeve 24 (e.g., proximal to distal release or distal to proximal release) at the time of implantation, as will be described in more detail with respect to FIGS. 14-18.

In yet another embodiment the inner tubular shaft 104 may include a proximal opening and a distal opening (or more than two openings) for allowing the thread 124 to enter and/or exit the lumen 122 of the inner tubular member 104 at different locations. In some cases, the thread 124 may extend distally through the lumen 122, exit through one of the two or more openings, wind around the sleeve 24, re-enter the lumen 122 through another (different) of the two or more openings, and extend distally through the lumen 122. In such an instance, both free ends of the thread 124 may be actuatable at the proximal end of the delivery device 100. For example, proximal pulling of one end of the thread 124 may result in proximal to distal deployment of the sleeve 24 while proximal pulling of the other end of the thread 124 may result in distal to proximal deployment of the sleeve 24. It is contemplated that the ends of the thread 124 may be identified with a marking to indicate which direction the sleeve 24 would be deployed upon actuation of the respective end of the thread 124.

Figure 10:
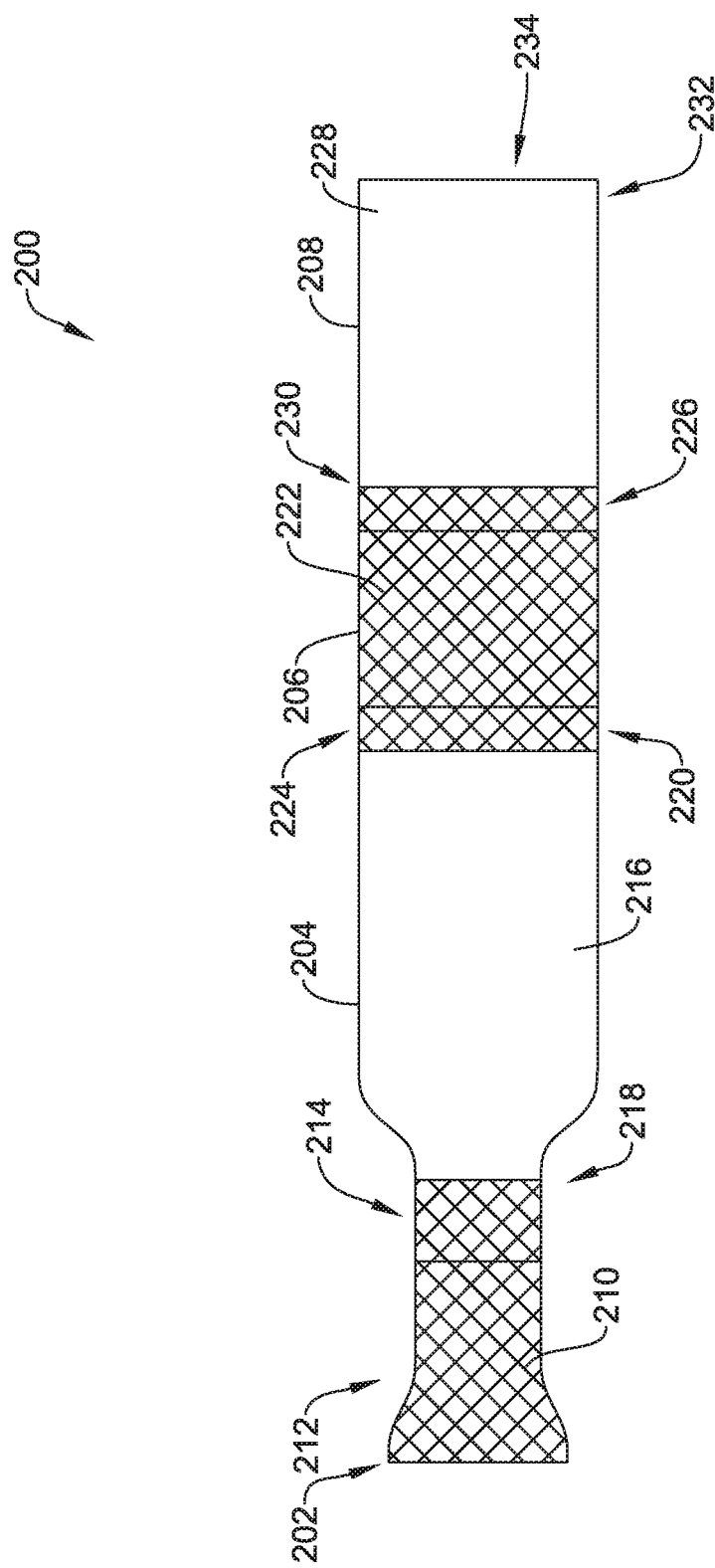
FIG. 10 illustrates a side view of another illustrative implant

FIG. 10 illustrates a side view of another illustrative implant 200 including a plurality of rigid and flexible portions. In the illustrated embodiment, the implant 200 may include a first stent portion 202, a first sleeve portion 204, a second stent portion 206, and a second sleeve portion 208. Thus, the sleeve portions 204 may alternate with the stent portions along a length of the implant 200. However, it is contemplated that the implant 200 may include any number of rigid and flexible regions desired. It is further contemplated that the rigid and flexible portions may be arranged in any order and/or pattern desired.

In some cases, the first stent portion 202 may include an elongated tubular stent frame 210. The stent 202 may be may be entirely, substantially or partially, covered with a polymeric covering, such as a coating (not explicitly shown). The covering may be disposed on an inner surface and/or outer surface of the stent 202, as desired. When so provided a polymeric covering may reduce or eliminate tissue ingrowth and/or reduce food impaction. The stent 202 may include regions of differing diameters. For example, the stent 202 may include a flared (e.g., enlarged relative to other portions of the stent 202) proximal end region 212. While not explicitly shown, the distal end region 214 of the stent 202 may also include a flared end region. The stent frame 210 may be radially expandable between a radially collapsed delivery configuration and a radially expanded configuration. The expanded configuration may secure the implant 200 at the desired location in a body lumen.

The second first stent portion 206 may include an elongated tubular stent frame 222. The stent 206 may be may be entirely, substantially or partially, covered with a polymeric covering or coating (not explicitly shown). The coating may be disposed on an inner surface and/or outer surface of the stent 206, as desired. When so provided a polymeric covering, such as a coating, may reduce or eliminate tissue ingrowth and/or reduce food impaction. The stent 206 may include regions of differing diameters. For example, while not explicitly shown the stent 206 may include a flared (e.g., enlarged relative to other portions of the stent 206) proximal end region 224 and/or a flared distal end region 226. The stent frame 222 may be radially expandable between a radially collapsed delivery configuration and a radially expanded configuration. The expanded configuration may secure the implant 200 at the desired location in a body lumen. In some cases, the implant 200 may include features (e.g., anti-migration flares, fixation spikes, sutures, etc.) to prevent distal/proximal displacement and/or migration of the implant 200, once the implant 200 is positioned and expanded in the body lumen.

The stent frames 210, 222 may have a woven structure, fabricated from a number of filaments. In some embodiments, the stent frames 210, 222 may be braided with one filament. In other embodiments, the stent frames 210, 222 may be braided with several filaments, as is found, for example, in the WallFlex®, WALLSTENT®, and Polyflex® stents, made and distributed by Boston Scientific. In another embodiment, the stent frames 210, 222 may be knitted, such as the Ultraflex™ stents made by Boston Scientific. In yet another embodiment, the stent frames 210, 222 may be of a knotted type, such the Precision Colonic™ stents made by Boston Scientific Scimed, Inc. In still another embodiment, the stent frames 210, 222 may be laser cut, such as the EPIC™ stents made by Boston Scientific. It is further contemplated that the stent frames 210, 222 may be fabricated in the same manner or different manners to provide differing properties a long a length of the implant 200, as desired.

It is contemplated that the stent frames 210, 222 can be made from a number of different materials such as, but not limited to, metals, metal alloys, shape memory alloys and/or polymers, as desired, enabling the stents 202, 206 to be expanded into shape when accurately positioned within the body. In some instances, the material may be selected to enable the stents 202, 206 to be removed with relative ease as well. For example, the stent frames 210, 222 can be formed from alloys such as, but not limited to, nitinol and Elgiloy®. Depending the on material selected for construction, the stents 202, 206 may be self-expanding (i.e., configured to automatically radially expand when unconstrained). In some embodiments, fibers may be used to make the stent frames 210, 222, which may be composite fibers, for example, having an outer shell made of nitinol having a platinum core. It is further contemplated the stent frames 210, 222 may be formed from polymers including, but not limited to, polyethylene terephthalate (PET). In some embodiments, the stents 202, 206 may be self-expanding while in other embodiments, the stents 202, 206 may be expand by an expansion device (such as, but not limited to a balloon inserted within the lumen of the stent(s) 202, 206). As used herein the term "self-expanding" refers to the tendency of the stent to return to a preprogrammed diameter when unrestrained from an external biasing force (for example, but not limited to a delivery catheter or sheath). One or both of the stents 202, 206 may include a one-way valve, such as an elastomeric slit valve or duck bill valve, positioned within the lumen thereof to prevent retrograde flow of gastrointestinal fluids.

In some cases, the first sleeve 204 may include a flexible membrane 216. While not explicitly shown, the sleeve 204 may include a support similar in form and function to the support 28 described herein with respect to FIG. 1. The sleeve 204 may be connected, affixed, or secured to the distal end region 214 of the first stent 202 adjacent to a proximal end region 218 of the sleeve 204. The sleeve 204 may be connected, affixed, or secured to the proximal end region 224 of the second stent 206 adjacent to a distal end region 220 of the sleeve 204. In some cases, the sleeve 204 may extend into a lumen of one or both of the stents 202, 206, although this is not required. In other embodiments, the sleeve 204 may extend partially, substantially, or all of a length of the implant 200 and cover all other portions (exterior surface and/or interior surface) of the implant 200, including the stents 202, 206. The membrane 216 may couple the sleeve 204 to one or both of the stents 202, 206. In some cases, the membrane 216 may be secured by an adhesive or other methods known in the art, including by not limited to thermal methods, mechanical methods, etc.

In some cases, the second sleeve 208 may include a flexible membrane 228. While not explicitly shown, the sleeve 208 may include a support similar in form and function to the support 28 described herein with respect to FIG. 1. The sleeve 208 may be connected, affixed, or secured to the distal end region 226 of the second stent 206 adjacent to a proximal end region 230 of the sleeve 208. In some cases, the sleeve 208 may extend into a lumen of the stent 206, although this is not required. In other embodiments, the sleeve 208 may extend partially, substantially, or all of a length of the implant 200 and cover all other portions (exterior surface and/or interior surface) of the implant 200, including the stents 202, 206. The membrane 228 may couple the sleeve 208 to one or both of the stents 202, 206. In some cases, the membrane 228 may be secured by an adhesive or other methods known in the art, including by not limited to thermal methods, mechanical methods, etc.

The sleeves 204, 208 may have an elongated, tubular shape with an interior lumen. Lumens of each of the stents 202, 206, and sleeves 204, 208 may be fluidly coupled to form a lumen 234 extending from the proximal end region 212 of the first stent 202 to the distal end region 232 of the second sleeve 208. In one example, the implant 200 defines only one interior lumen. However, other embodiments including more than one lumen are contemplated. In an expanded configuration, the sleeves 204, 208 may be substantially cylindrical, although this is not required. Absent a support, the membranes 216, 228 may be flexible, thin membranes that readily collapses on themselves. However, if so provided, supports may provide rigidity and structure to sleeves 204, 208. Some examples and discussion of illustrative supports may be found in Patent Application No. 62/419,707, filed on Nov. 9, 2016, titled DEPLOYABLE SLEEVES AND RELATED METHODS, the disclosure of which is incorporated herein by reference.

The membranes 216, 228 may include one or more of the following polymer materials: polyethylene, polypropylene, polystyrene, polyester, biosorbable plastics (e.g., polylactic acid), polycarbonate, polyvinyl chloride, polyacrylate, acrylate, polysulfone, polyetheretherketone, thermoplastic elastomers, thermoset elastomers (e.g., silicone), poly-p-xylylene (parylene), flouropolymers (e.g., polytetrafluoroethylene (PTFE), polyvinylidene fluoride (PVDF), poly(vinylidene fluoride-co-hexafluoropropylene) (PVDFHFP)), bioplastics (e.g., cellulose acetate). The sleeve may additionally or alternatively include one or more of: polyurethane and its copolymers, ethylene vinyl-acetate, polyethylene terephthalate (PET), polyolefins, cellulosics, polyamides, acrylonitrile butadiene styrene copolymers, styrene isoprene butadiene (SIBS) block copolymers, acrylics, poly(glycolide-lactide) copolymer, Tecothane, PEBAX, poly(γ-caprolactone), poly(γ-hydroxybutyrate), polydioxanone, poly(γ-ethyl glutamate), polyiminocarbonates, poly(ortho ester), and/or polyanhydrides. Blends of the above polymers may also be employed.

In further detail, the implant 200 may be generally cylindrical in shape, although this is not required, substantially flexible, and sized appropriately for a convenient accommodation within the digestive tract. It is contemplated that various shapes, sizes and designs of the implant may be constructed depending on the size and geometry of the cavities where the implant 200 has to be placed. In various examples, the implant may have a length between 3-12 inches, 3-6 inches, 0.5-20 feet (0.15-6.1 meters), between 3-5 feet (0.9-1.5 meters), or about 2-4 feet (0.6-1.2 meters). However, the implant 200 may have a length of less than 0.5 feet (0.15 meters) or greater than 20 feet (6.1 meters).

Once implanted in a patient, one or both of the stent 202, 206 may exert a radially outward force to help secure the implant 200 to the body lumen. The implant 200 may be positioned in the esophagus, the gastro-esophageal junction (GEJ) region, or at or near the pylorus with the sleeve(s) 204, 208 extending through the stomach or other portions of the gastro-intestinal system. In another example, the implant 200 may be positioned in the patient's intestine. In some examples, the implant 200 does not include one or both of the stent 202, 206. Instead, the sleeve(s) 204, 208 may be secured directly to the patient's tissue using sutures or any other suitable attachment mechanism.

Figure 11:
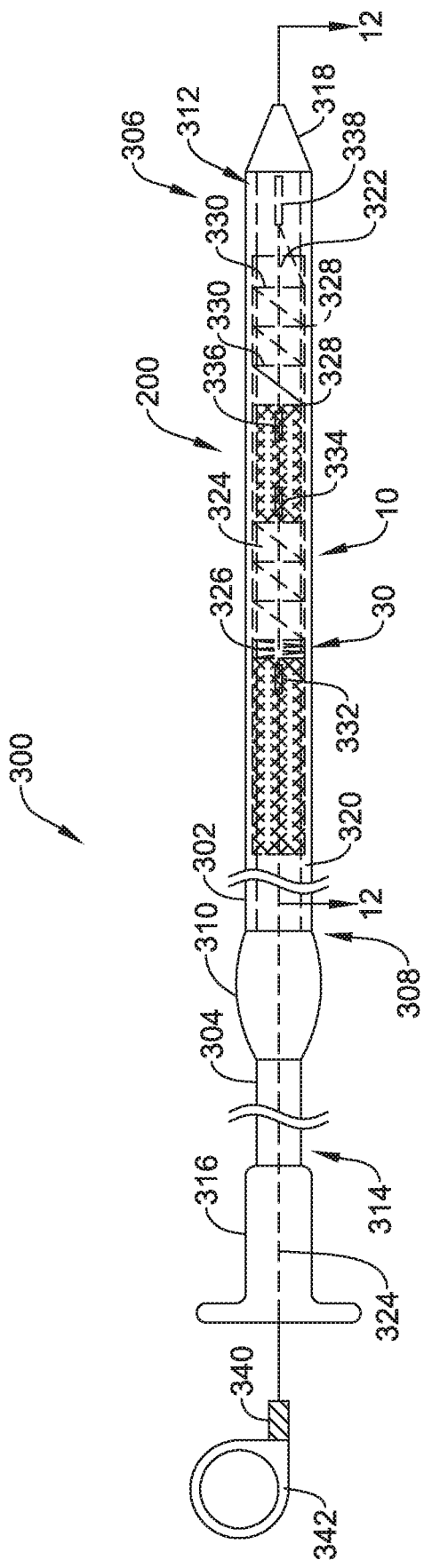
FIG. 11 is a side view of an illustrative delivery system for delivering the implant of FIG. 10.

FIG. 11 is a side view of an illustrative delivery system 300 for delivering an implant having both a rigid portion and a flexible portion, such as any of the implants described herein, to a target region. The delivery system 300 may include an outer or exterior elongate shaft or tubular member 302 and an inner elongate shaft or tubular member 304. The inner tubular member 304 may be slidably disposed within a lumen of the outer tubular member 302. The outer tubular member 302 may extend proximally from a distal end region 306 to a proximal end region 308 configured to remain outside of a patient's body. A first hub or handle 310 may be coupled to the proximal end region 308 of the outer tubular member 302. The inner tubular member 304 may extend proximally from a distal end region 312 to a proximal end region 314 configured to remain outside of a patient's body during an implantation procedure. A second hub or handle 316 may be coupled to the proximal end region 314 of the inner tubular member 304. The inner tubular member 304 may further include a distal tip 318 positioned adjacent to the distal end region 312. The distal tip 318 may be configured to be atraumatic.

The outer tubular member 302 may include a lumen 320 extending from the distal end region 306 to the proximal end region 308. The lumen 320 may also extend through the first handle 310. The lumen 320 of the outer shaft 302 and the first handle 310 may be configured to slidably receive the inner shaft 304. The inner tubular member 304 may include a lumen 322 extending from the distal end region 312 to the proximal end region 314. The lumen 322 of the inner tubular shaft 304 may extend through the second handle 316. The lumen 322 of the inner shaft 304 may be configured to receive a thread, pull-wire and/or guidewire, as desired.

The implant 200 may be disposed around a portion of the inner tubular member 304 at or adjacent to the distal end region 312 thereof. When the implant 200 is disposed over the inner tubular member 304, in a delivery configuration, the stent portions 202, 206 may be restrained in a collapsed reduced diameter or delivery configuration by the outer tubular member 302 surrounding the stent portions 202, 206. In some cases, the outer tubular member 302 may be configured to extend over the entire length of the implant 200. The distal end region 306 of the outer tubular member 302 may be positioned such that the outer tubular member 302 surrounds and covers at least the length of stent portions 202, 206 during delivery. The outer tubular member 302 may have sufficient hoop strength to retain the stents 202, 206 in their reduced diameter state.

The sleeves 204, 208 may be held in a radially collapsed configuration through the use of a thread 324 (e.g., filament or wire). The thread 324 may be any thin flexible element capable of being wrapped and unwrapped about the sleeves 204, 208. The thread 324 may be wound about an outer surface of the sleeves 204, 208 to apply a biasing force to the sleeves 204, 208 which maintains the sleeves 204, 208 in a collapsed or reduced diameter configuration. In some embodiments, a distal end 326 of the thread 324 may be positioned adjacent to the proximal end region 224 of the first sleeve 204. In other embodiments, the distal end 326 of the thread 324 may be positioned adjacent to the distal end region 232 of the second sleeve 208 as described in more detail with respect to FIG. 13. It is contemplated that the position of the distal end 326 of the thread 324 may determine which portion of the sleeve 204 (e.g., proximal or distal) is expanded first and/or which sleeve 204, 208 is deployed first. In some cases, the thread 324 may wound such that the clinician may have the option of selecting which portion of the sleeves 204, 208 and/or which sleeve 204, 208 is deployed first.

The thread 324 may be wrapped around the sleeves 204, 208 in a generally helical manner, although this is not required. The spacing of adjacent windings 330 of the thread 124 may be uniform or variable as desired. In other words the pitch of the windings 330 may be the same, varied, or combinations thereof, as desired. In some cases, the thread 324 may include a plurality of knots 328 similar in form and function to those used in knitting or crocheting, which allow the thread 324 to be releasably secured about the sleeves 204, 208. The knots 328 may generally maintain the thread 324 in a desired configuration while still allowing the thread to be unraveled or removed as desired. In some cases, the thread 324 may not include knots 328.

The thread 324 may extend through one or more skives, slots, or other openings 332, 334, 336, 338 to enter and exit the lumen 322 of the inner tubular member 304, as desired, as will be described in more detail with reference to FIG. 12. The openings 332, 334, 336, 338 may extend from an outer surface to an inner surface of the inner tubular member 304 to allow the thread 324 (or other components, as desired) to extend between the exterior of the inner tubular member 304 and the interior thereof. The openings 332, 334, 336, 338 may be spaced along a length of the inner tubular member 304. The openings 332, 334, 336, 338 may be positioned in line with one another (e.g., sharing a common axis). It is contemplated that the thread 324 may be woven in and out of the slots or openings 332, 334, 336, 338 to be selectively wrapped around the sleeves 204, 208 of the implant 200 while leaving an outer surface of the stents 202, 206 generally or substantially free from the thread 324. Thus, the thread 324 may be positioned radially inward of the stents 202, 206. For example, the thread 324 may pass through the stents 202, 206 to enter and/or exit an opening 332, 334, 336, 338 but may not be disposed about the stents 202, 206 (e.g., radially outward of the stents 202, 206) in a manner or extent sufficient to maintain the stent 202, 206 in a collapsed configuration absent the outer tubular member 302. The thread 324 may extend proximally through the lumen 322 and exit proximally at the second handle 316. The proximal end 340 of the thread 324 may be coupled to or otherwise affixed to a pull member 342 or other actuation mechanism. The pull member 342, such as a pull ring, a pull tab, or the like, may facilitate actuation of thread 324; however a pull member 342 or other actuation mechanism may not be present or required.

Figure 12:
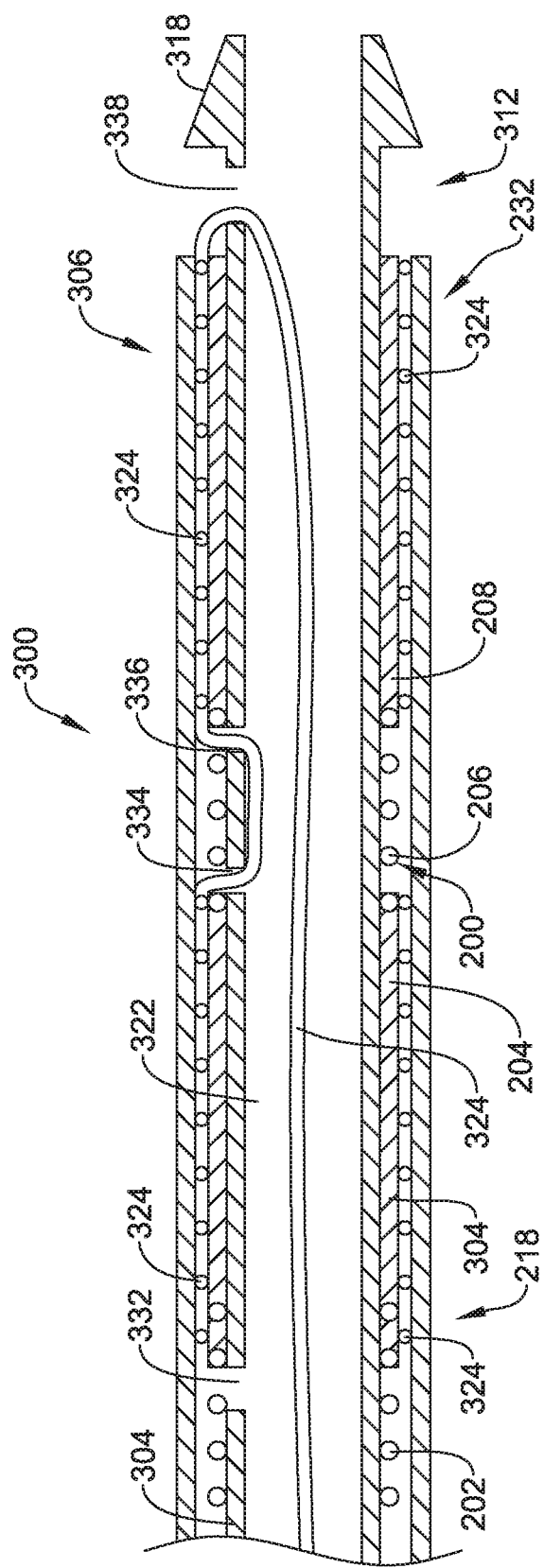
FIG. 12 is a close up side view of the illustrative delivery system of FIG. 11 in an illustrative delivery configuration.

FIG. 12 illustrates a close up side view of a distal portion of the delivery device 300 with the implant 200 in a radially collapsed or delivery configuration. The delivery device 300 may be advanced through the gastrointestinal tract transorally or transrectally, as desired. The delivery device 300 may be advanced with or without the use of a guidewire. Once the implant 200 is positioned adjacent to the target region, the restraining forces maintaining the stents 202, 206 and the sleeves 204, 208 in the radially collapsed configuration may be removed either in series (one after the other) or simultaneously (e.g., together) to deploy the implant 200.

As can be seen in more detail in FIG. 12, the thread 324 may extend distally from its proximal end 340 through the lumen 322 of the inner tubular member 304. The thread 324 may exit the lumen 322 through the distal-most opening, or fourth opening, 338. The thread 324 may then wind around the second sleeve 208 in a proximal direction (e.g. from distal to proximal). The thread 324 may re-enter the lumen 322 through a third opening 336 (e.g., proximal to the fourth opening 338). In some cases, the third opening 336 may be positioned beneath (radially inward of) the second stent 206. In such an instance, the thread 324 may pass between portions of the stent frame 222 and into the lumen 322. The thread 324 may extend proximally within the lumen 322 and exit the lumen 322 through a second opening 334 (e.g., proximal to the third opening 336). The thread 324 may then wind around the first sleeve 204 in a proximal direction (e.g. from distal to proximal). A distal end 326 of the thread 324 may be positioned adjacent to the proximal end region 218 of the first sleeve 204. While the first and second sleeves 204, 208 are illustrated as two separate and distinct elements, it is contemplated that the first and second sleeves 204, 208 may be formed from a single unitary membrane that extend along the second stent 206 and/or the first stent 202, as desired.

In an implant having a plurality of sections 202, 204, 206, 208, it may be desirable to deploy the rigid stent portions 202, 206 first, followed by the flexible sleeve portions 204, 208. The stents 202, 206 may be deployed by actuating the first handle 310 proximally relative to the second handle 316, e.g., by pulling the first handle 310 (see, for example, FIG. 11) proximally while maintaining the second handle 316 in a fixed position. Thus, the outer tubular shaft 302 may be retracted proximally relative to the inner tubular shaft 304. In other words, the outer tubular shaft 302 may be proximally retracted while the inner tubular shaft 304 is held stationary. As the outer tubular shaft 302 is retracted proximally to uncover the stents 202, 206, the biasing force is removed from the exterior of the stents 202, 206 and the stents 202, 206 assume their radially expanded, unbiased, deployed configuration while the sleeves 204, 208 remain in the collapsed configuration under the biasing force of the thread 324. Once the stents 202, 206 have been deployed, the sleeves 204, 208 may be deployed.

A proximal or pulling force may be applied to the proximal end 340 of the thread 324. In some cases, the pulling force may be applied by placing a finger inside of the pull member 342 and pulling away from the handle 316. As the member 342 is pulled or actuated, the thread 324 begins to uncoil or unravel. In the embodiment shown in FIG. 12, the thread 324 is wrapped or wound such that the thread 324 disposed over the distal portion 232 of the second sleeve 208 is removed or unraveled first. As the biasing force of the thread 324 is released, the second sleeve 208 begins to expand into its unbiased or deployed configuration in a distal to proximal direction. As the thread 324 is pulled, the portion of the thread 324 previously wound around the second sleeve 208 unravels and enters the lumen 322 through the fourth opening 338. The thread 324 then moves proximally through the lumen 322. Continued unraveling of the thread 324 will cause more of the length of the second sleeve 208 to be released, followed by the first sleeve 204 (in a distal to proximal direction). Proximal actuation of the proximal end 340 of the thread 324 may continue until the distal end 326 of the thread 324 has been completely unraveled and both the first and second sleeves 204, 208 are deployed. It is contemplated that the clinician may continue to pull the thread 324 until the distal end 326 has been completely removed from the lumen 322 and the device 300 although this is not required. The entire delivery device 300 may then be removed from the body lumen.

Figure 13:
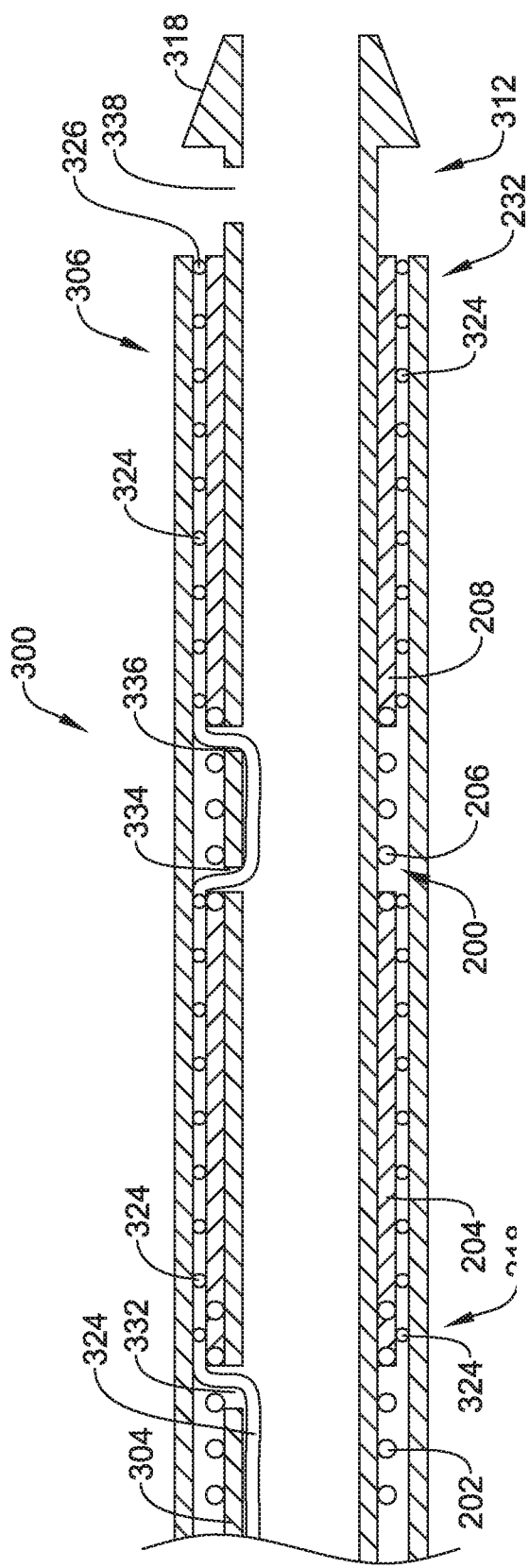
FIG. 13 is another close up side view of the illustrative delivery system of FIG. 11 in another illustrative delivery configuration.

FIG. 13 illustrates another close up side view of a distal portion of the delivery device 300 with the implant 200 in a radially collapsed or delivery configuration. The delivery device 300 may be advanced through the gastrointestinal tract transorally or transrectally, as desired. The delivery device 300 may be advanced with or without the use of a guidewire. Once the implant 200 is positioned adjacent to the target region, the restraining forces maintaining the stents 202, 206 and the sleeves 204, 208 in the radially collapsed configuration may be removed either in series (one after the other) or simultaneously (e.g., together) to deploy the implant 200.

As can be seen in more detail in FIG. 13, the thread 324 may extend distally from its proximal end 340 through the lumen 322 of the inner tubular member 304. The thread 324 may exit the lumen 322 through the proximal-most opening, or first opening, 332. In some cases, the first slot 332 may be positioned beneath (radially inward of) the first stent 202. In such an instance, the thread 324 may pass between portions of the stent frame 210 and out of the lumen 322. The thread 324 may then wind around the first sleeve 204 in a distal direction (e.g. from proximal to distal). The thread 324 may re-enter the lumen 322 through a second slot 334 (e.g., distal to the first slot 332). In some cases, the second slot 334 may be positioned below the second stent 206. In such an instance, the thread 324 may pass between portions of the stent frame 222 and into the lumen 322. The thread 324 may extend distally within the lumen 322 and exit the lumen 322 through a third opening 336 (e.g., distal to the second opening 334). The thread 324 may then wind around the second sleeve 208 in a distal direction (e.g. from proximal to distal). A distal end 326 of the thread 324 may be positioned adjacent to the distal end region 232 of the second sleeve 208. While the first and second sleeves 204, 208 are illustrated as two separate and distinct elements, it is contemplated that the first and second sleeves 204, 208 may be formed from a single unitary membrane that extend along the second stent 206 and/or the first stent 202, as desired.

In an implant having a plurality of sections 202, 204, 206, 208, it may be desirable to deploy the rigid stent portions 202, 206 first, followed by the flexible sleeve portions 204, 208. The stents 202, 206 may be deployed by actuating the first handle 310 proximally relative to the second handle 316, e.g., by pulling the first handle 310 (see, for example, FIG. 11) proximally while maintaining the second handle 316 in a fixed position. Thus, the outer tubular shaft 302 may be retracted proximally relative to the inner tubular shaft 304. In other words, the outer tubular shaft 302 may be proximally retracted while the inner tubular shaft 304 is held stationary. As the outer tubular shaft 302 is retracted proximally to uncover the stents 202, 206, the biasing force is removed from the exterior of the stents 202, 206 and the stents 202, 206 assume their radially expanded, unbiased, deployed configuration while the sleeves 204, 208 remain in the collapsed configuration under the biasing force of the thread 324. Once the stents 202, 206 have been deployed, the sleeves 204, 208 may be deployed.

A proximal or pulling force may be applied to the proximal end 340 of the thread 324. In some cases, the pulling force may be applied by placing a finger inside of the pull member 342 and pulling away from the handle 316. As the member 342 is pulled or actuated, the thread 324 begins to uncoil or unravel. In the embodiment shown in FIG. 13, the thread 324 is wrapped or wound such that the thread 324 disposed over the proximal portion 218 of the first sleeve 204 is removed or unraveled first. As the biasing force of the thread 324 is released, the first sleeve 204 begins to expand into its unbiased or deployed configuration in a proximal to distal direction. As the thread 324 is pulled, the portion of the thread 324 previously wound around the first sleeve 204 unravels and enters the lumen 322 through the first opening 332. The thread 324 then moves proximally through the lumen 322. Continued unraveling of the thread 324 will cause more of the length of the first sleeve 204 to be released, followed by the second sleeve 208 (in a proximal to distal direction). Proximal actuation of the proximal end 340 of the thread 324 may continue until the distal end 326 of the thread 324 has been completely unraveled and both the first and second sleeves 204, 208 are deployed. It is contemplated that the clinician may continue to pull the thread 324 until the distal end 326 has been completely removed from the lumen 322 and the device 300 although this is not required. The entire delivery device 300 may then be removed from the body lumen.

During implantation, the stent may be implanted through endoscopic procedures, and therefore, they may be mounted on a delivery device for delivery under direct vision and/or under fluoroscopy. Radiopaque markers positioned on the implant 10, 200 or delivery device 100, 300, may enable an operator to ascertain whether the implant 10, 200 is in a desirable location, optimal, and safe. Finally, once the stent is positioned, the operator may retract and/or remove, the delivery device.

Figure 14:
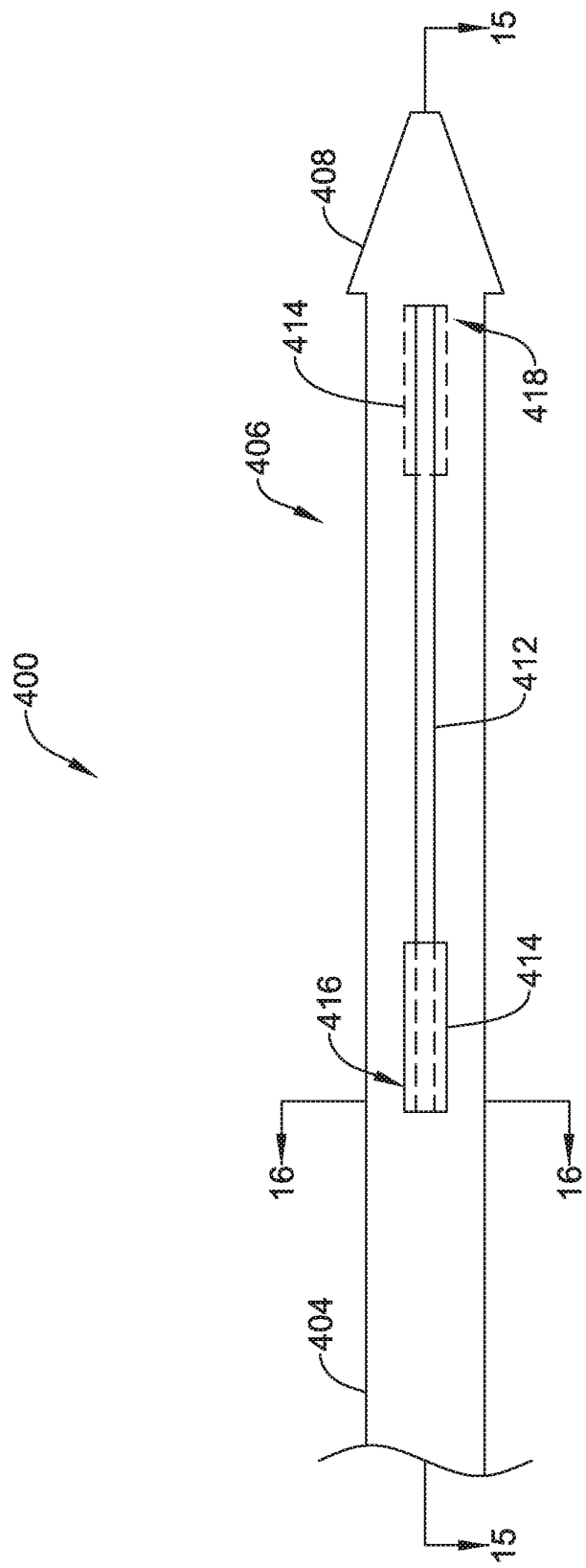
FIG. 14 is a side view of another illustrative delivery system for delivery an implant.
Figure 15:
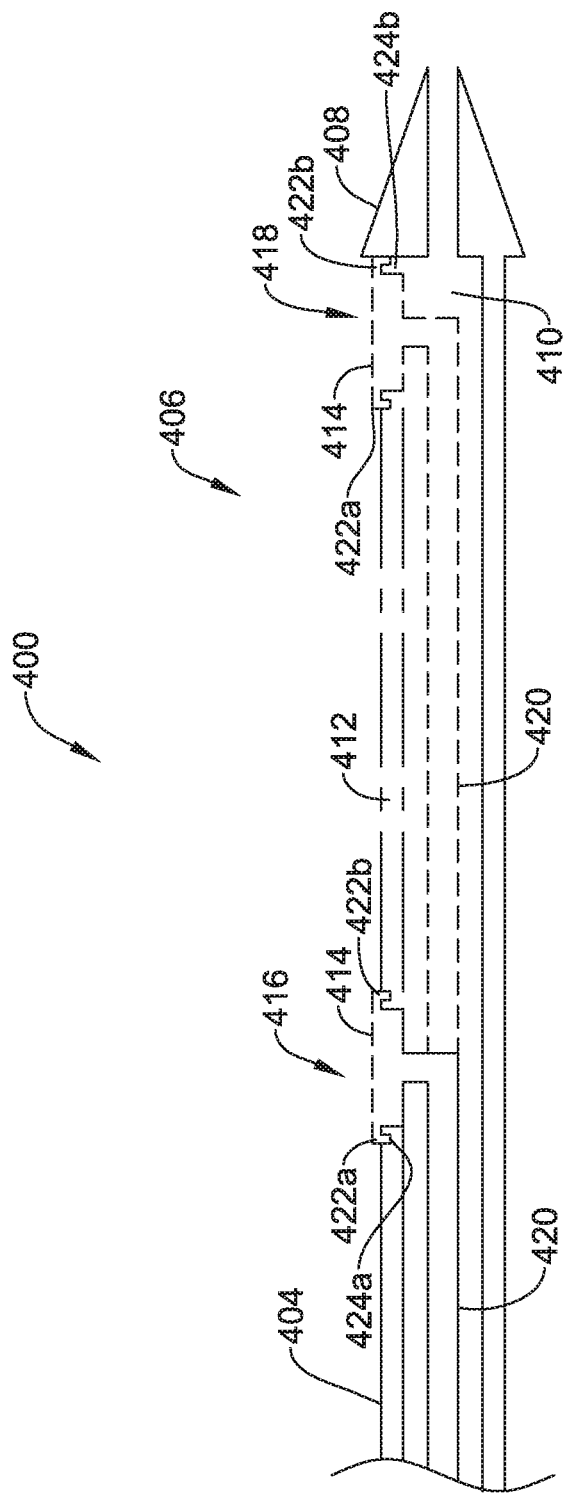
FIG. 15 is a cross-sectional view of the illustrative delivery system of FIG. 14, taken at line 15-15.

FIG. 14 illustrates a distal end region of another illustrative delivery system 400 for delivering an implant having both a rigid portion and a flexible portion, such as the implant 10 described herein, to a target region. FIG. 15 is a cross-sectional view of the illustrative delivery system 400 taken at line 15-15 of FIG. 14. The illustrative delivery system 400 may be configured to include a sliding element to allow for a clinician to intraoperatively select a direction of expansion for the flexible portion of the implant (e.g., distal to proximal as described with respect to FIGS. 3-7 or proximal to distal as described with respect FIGS. 8-9).

The delivery system 400 may include an outer or exterior elongate shaft or tubular member 402 (see, for example, FIGS. 18-20) and an inner elongate shaft or tubular member 404. The inner tubular member 404 may be slidably disposed within a lumen of the outer tubular member. The outer tubular member may be similar in form and function to the outer tubular member 102 described herein. The outer tubular member may extend proximally from a distal end region to a proximal end region configured to remain outside of a patient's body. A first hub or handle, similar in form and function the handle 110 described herein, may be coupled to the proximal end region of the outer tubular member. The inner tubular member 404 may extend proximally from a distal end region 406 to a proximal end region (not explicitly shown) configured to remain outside of a patient's body during an implantation procedure. A second hub or handle, similar in form and function to the second handle 116 described herein, may be coupled to the proximal end region of the inner tubular member 404. The inner tubular member 404 may further include a distal tip 408 positioned adjacent to the distal end region 112. The distal tip 408 may be configured to be atraumatic.

The inner tubular member 404 may include a lumen 410 extending from the distal end region 112 to the proximal end region 114. The lumen 410 of the inner tubular shaft 404 may also extend through the second handle. The lumen 410 of the inner shaft 404 may be configured to receive a thread, pull-wire and/or guidewire, as desired.

The inner tubular member 404 may include a slot 412 extending along a portion of the length thereof at or adjacent to the distal portion 406. In some embodiments, the slot 412 may have a length similar to a length of the flexible portion of the implant, such as the implant 10 described herein, although this is not required. A sliding skive 414 may be slidably positioned within the slot 412. The sliding skive 414 may be configured to move between first position adjacent the proximal end 416 of the slot and a second position (illustrated in phantom) adjacent the distal end 418 of the slot 412. In some cases, the sliding skive 414 may be positioned at an intermediate location between the proximal end 416 and the distal end 418, although this is not required.

The sliding skive 414 may be actuated by means of a slider 420, or other actuation mechanism, positioned with the lumen 410 of the inner tubular member 404. The slider 420 may extend proximally to a point outside of the body such that the sliding skive 414 can be moved (e.g., pushed distally or pulled proximally) along the slot 412 by the clinician. In some embodiments, the sliding skive 414 may include a first protrusion 422a positioned adjacent a proximal end of the sliding skive 414 and a second protrusion 422b adjacent the distal end of the sliding skive 414. It is contemplated that the protrusions 422a, 422b may be configured to engage a mating recess 424a, 424b adjacent the proximal end 416 and/or the distal end 418 of the slot 412 to allow the sliding skive 414 to be releasably fixed in a desired position. It is contemplated that the protrusions 422a, 422b may be positioned at any surface of the sliding skive 414 desired. Similarly, the mating recesses 424a, 424b may be positioned at any location on the inner tubular member 404 (e.g., an inner surface and/or outer surface) to receive the protrusions 422a, 422b. Furthermore, the mating structures may be reversed in some instances.

Figure 16:
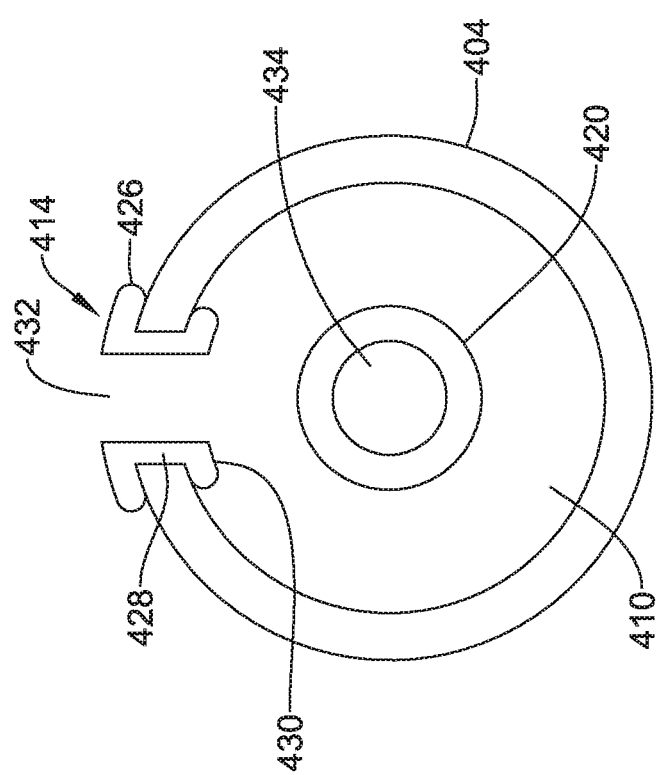
FIG. 16 is a cross-sectional view of the illustrative delivery system of FIG. 14, taken at line 16-16.
Figure 17:
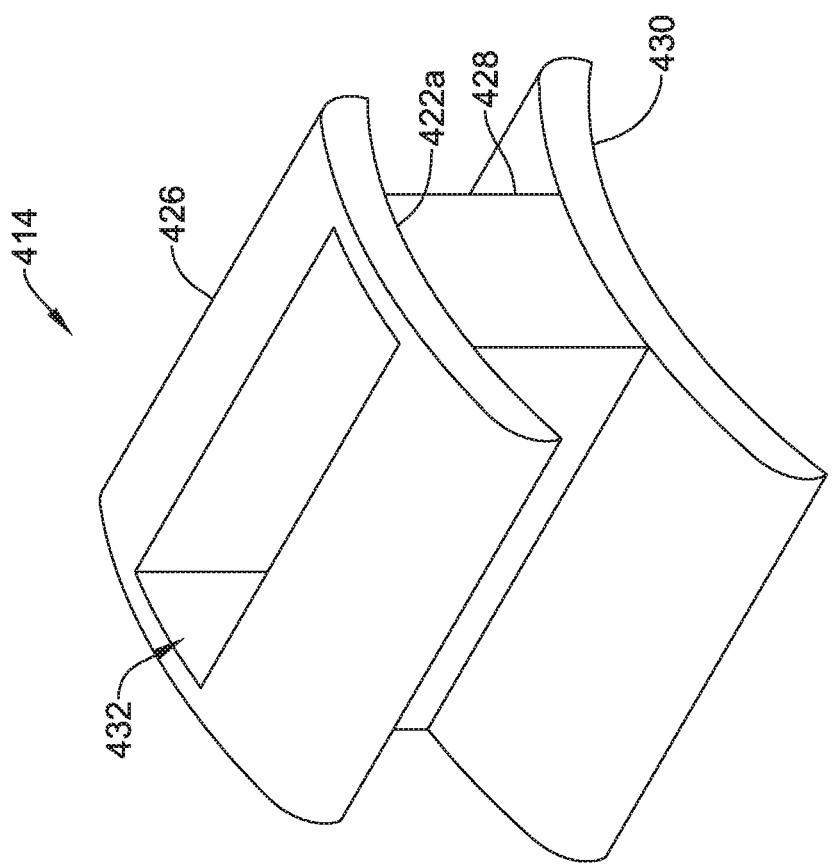
FIG. 17 is a perspective view of an illustrative sliding component configured to be used with the illustrative delivery system of FIG. 14.

FIG. 16 illustrates a cross-sectional view (not to scale) of the illustrative delivery device 400 taken at line 16-16 of FIG. 14. FIG. 17 illustrates a proximal perspective view of the illustrative sliding skive 414. The sliding skive 414 may be sized and shaped to slide longitudinally within the slot 412 while including retention features configured to prevent the sliding skive 414 from uncoupling from the inner tubular member 404. For example, the sliding skive 414 may include a top portion 426 configured to move along an outer surface of the inner tubular member 404, an intermediate portion 428 configured to within the slot 412, and a bottom portion 430 configured to move along an inner surface of the inner tubular member 404. The top and bottom portions 426, 430 may have a width dimension greater than a width of the slot 412 and/or a width of the intermediate portion 428 such that the sliding skive 414 is prevented from moving in the radial direction (e.g., disengaging the from the slot 412). A slot or through hole 432 may extend from a top surface of the top portion 426 to a bottom surface of the bottom portion 430. This may allow a thread (not explicitly shown) to pass from a location exterior to the inner tubular member 404 and into the lumen 410 thereof. In some cases, the thread may extend into a lumen 434 of the slide 420. The lumen 432 of the slider 420 may be configured to extend proximally from the sliding skive 414 to a location external of the patient's body to allow for actuation of the thread as described in more detail herein. It is further contemplated that the surfaces of the sliding skive 414 may be turned, smoothed or otherwise rounded to allow a thread to run easily over the surface, as will be described in more detail herein.

Figure 18:
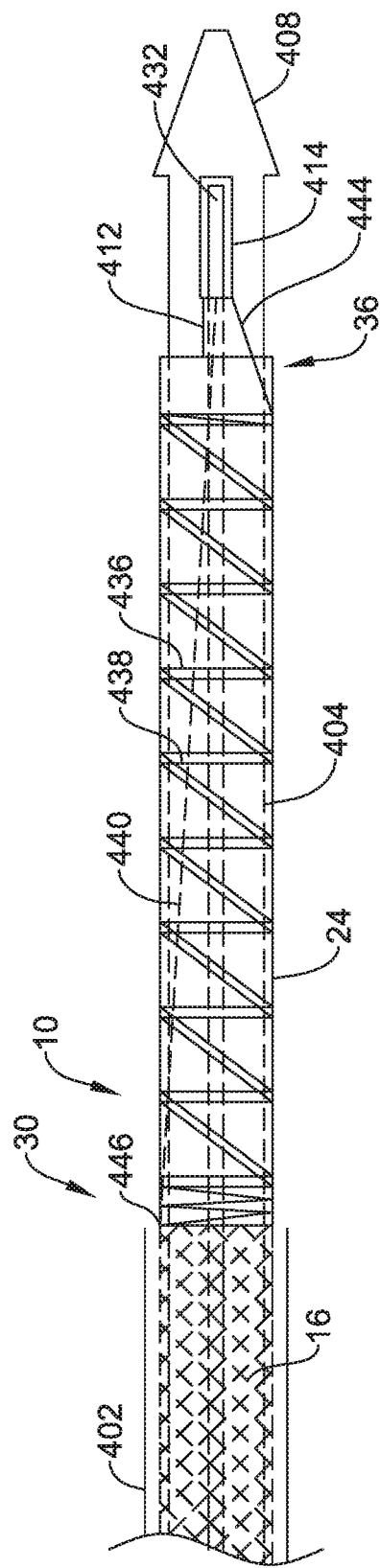
FIG. 18 is a side view of the illustrative delivery system of FIG. 14 in a first configuration for delivering the implant of FIG. 1.
Figure 19:
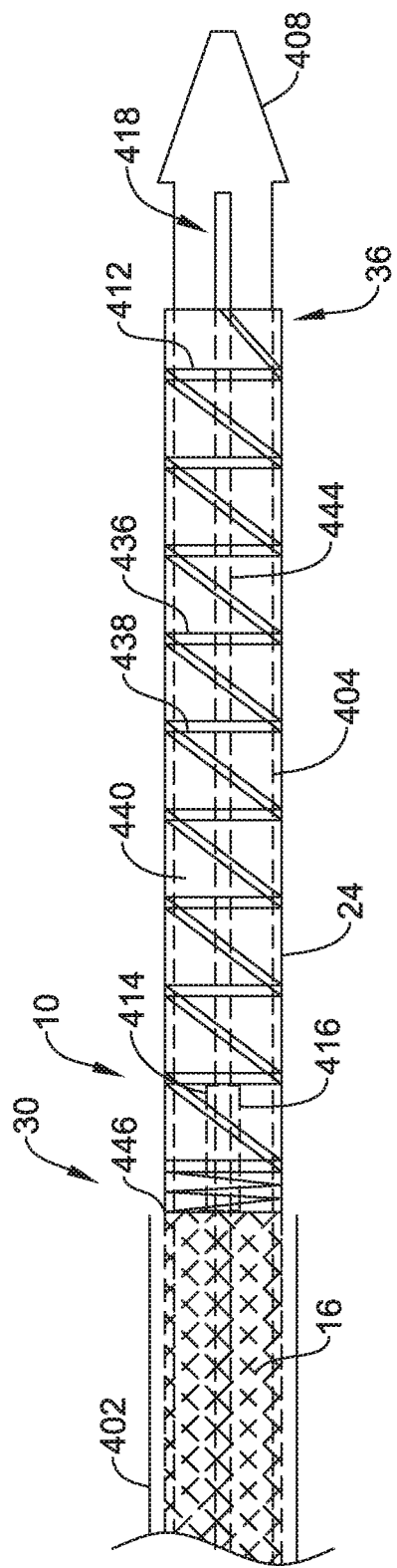
FIG. 19 is another side view of the illustrative delivery system of FIG. 14 in a second configuration for delivering the implant of FIG. 1.

FIGS. 18 and 19 illustrate the distal portion of the illustrative delivery system 400 having an implant 10 disposed over a portion of the inner tubular member 404 at or adjacent to the distal end region 406 thereof. When the implant 10 is disposed around the inner tubular member 404, in a delivery configuration, the stent portion 16 may be restrained in a radially collapsed reduced diameter or delivery configuration by the outer tubular member 402 surrounding the stent portion 16. The distal end region of the outer tubular member 402 may be positioned such that the outer tubular member 402 surrounds and covers the length of stent 16 during delivery. The outer tubular member 402 may have sufficient hoop strength to retain the stent 16 in its reduced diameter state.

The sleeve 24 may be held in a radially collapsed configuration through the use of two or more threads 436, 438 (e.g., filaments or wires). The threads 436, 438 may be any thin flexible element capable of being wrapped and unwrapped about the sleeve 24. A distal portion of the threads 436, 438 may be wound or wrapped about the sleeve 24 while a proximal portion of the thread 436, 438 may extend proximally through the lumen 410 or lumen 434 to a point outside the delivery device 400. The threads 436, 438 may be wound about an outer surface of the sleeve 24 to apply a biasing force to the sleeve 24 which maintains it in a collapsed or reduced diameter configuration.

The threads 436, 438 may be wound in opposite directions such that the threads 436, 438 may be released sequentially to allow for selective release of the sleeve 24. In some embodiments, a distal end 446 of a first thread 436 may be positioned adjacent to the proximal end region 30 of the sleeve 24 to allow for distal to proximal release in a manner similar to that described with respect to FIGS. 3-7. A distal end 442 of a second thread 438 may be positioned adjacent to the distal end region 36 of the sleeve 24 to allow for proximal to distal release in a manner similar to that described with respect FIGS. 8-9. The presence of two threads 436, 438 may allow the clinician to intraoperatively select which direction he or she desires to release the sleeve 24. The thread 436 or 438 that is wound in that direction may be removed second (e.g. after removal of the thread wound in the undesired deployment direction) to deploy the sleeve 24.

The threads 436, 438 may be wrapped around the sleeve 24 in a generally helical manner, although this is not required. The spacing of adjacent windings of the threads 436, 438 may be uniform or variable as desired. In other words the pitch of the windings may be the same, varied, or combinations thereof, as desired. In some cases, the threads 436, 438 may include a plurality of knots similar in form and function to those used in knitting or crocheting, which allow the threads 436, 438 to be releasably secured about the sleeve 24. The knots may generally maintain the threads 436, 438 in a desired configuration while still allowing the threads 436, 438 to be unraveled or removed as desired. In some cases, the threads 436, 438 may not include knots.

The threads 436, 438 may extend through the opening 432 in the sliding skive 414 into the lumen 410 of the inner tubular member 404 or the lumen 434 of the slider 420. The threads 436, 438 may extend proximally through the lumen 410 and exit proximally at a handle. The proximal ends of the threads 436, 438 are configured to remain outside of the inner tubular member 404 and may be coupled to or otherwise affixed to a pull member or other actuation mechanism. The pull member may facilitate actuation of threads 436, 438; however a pull member or other actuation mechanism may not be present or required. The sliding skive 414 may be positionable such that it is located nearest the portion of the thread 436, 438 that will be released first. This may prevent too much pressure from being applied to the inner tubular member 404 during device 10 deployment (a phenomenon known of 'bowing' can occur if too much pressure is applied while the knots are being pulled to open and deploy). The sliding arrangement may eliminate or significantly reduce this bowing. For example, in FIG. 18 the sliding skive 414 may be positioned adjacent to the distal end region 418 of the slot 412. As described above, the sliding skive 414 may be releasably secured through engagement of protrusions and grooves. This arrangement may allow for the release of the first thread 436. As can be seen, the sliding skive 414 is positioned nearest to the region 444 of the first thread 436 which is released from the sleeve 24 first (e.g., distal to proximal release). The second thread 438 may include some slack (or extra length) to allow for a region 440 of the thread 438 to pass under the sleeve 24 and into the sliding skive 414. Once the first thread 436 is released (e.g., in a manner similar to that described with respect to FIGS. 3-7), the sliding skive 414 may be slid to the proximal end 416 of the slot 412. As the second thread 438 is still in place, the sleeve 24 remains in its radially collapsed configuration. The second thread 438 may then be released (e.g., in a manner similar to that described with respect to FIGS. 8-9).

Alternatively, the second thread 438 may be released prior to the first thread 436. It should be noted that the use of "first" and "second" is not intended to limit the order of release of the threads 436, 438 but rather as a means of differentiating between the two threads 436, 438. In FIG. 19 the sliding skive 414 may be positioned adjacent to the proximal end region 416 of the slot 412. As described above, the sliding skive 414 may be releasably secured through engagement of protrusions and grooves. This arrangement may allow for the release of the second thread 438. As can be seen, the sliding skive 414 is positioned nearest to the region 440 of the second thread 438 which is released from the sleeve 24 first (e.g., proximal to distal release). The first thread 436 may include some slack (or extra length) to allow for a region 444 of the thread 436 to pass under the sleeve 24 and into the sliding skive 414. Once the second thread 438 is released (e.g., in a manner similar to that described with respect to FIGS. 8-9), the sliding skive 414 may be slid to the distal end 418 of the slot 412. As the first thread 436 is still in place, the sleeve 24 remains in its radially collapsed configuration. The first thread 436 may then be released (e.g., in a manner similar to that described with respect to FIGS. 3-7).

Figure 20:
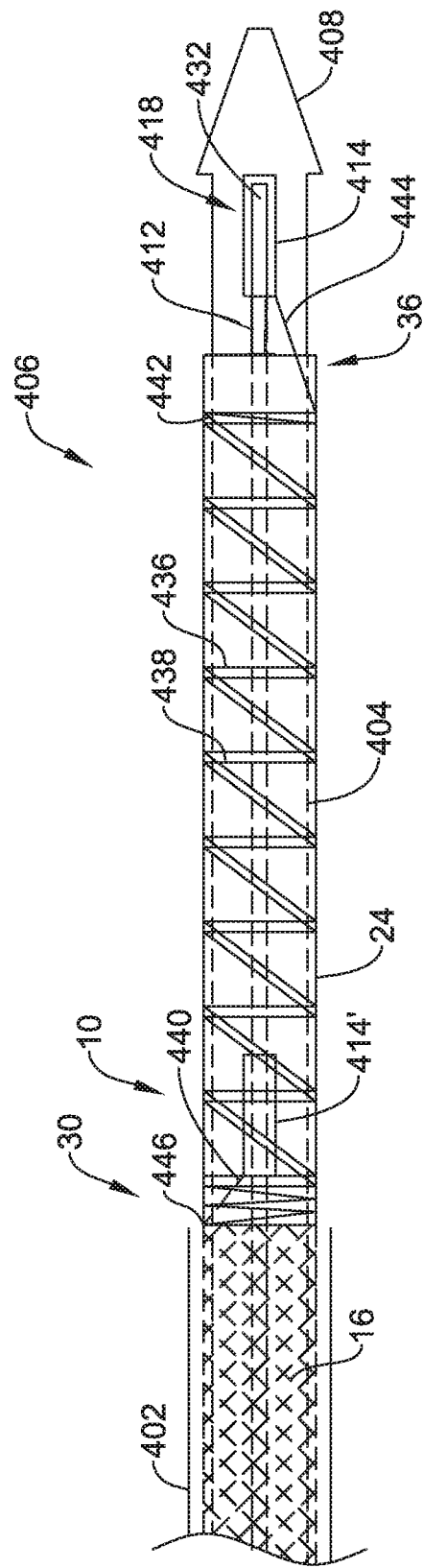
FIG. 20 is another side view of the illustrative delivery system of FIG. 14 in a third configuration for delivering the implant of FIG. 1.

Alternatively, or additionally, the delivery device 400 may be provided with a second sliding skive 414', as shown in FIG. 20. A first sliding skive 414 may be positioned adjacent the distal end 418 of the slot 412 and a second sliding skive 414' may be positioned adjacent the proximal end 416 of the slot 412. It is contemplated that instead of sliding skives 414, 414', the inner tubular member 404 may be provided with two slots (similar in form and function to the slot 132 described above). A first slot may be positioned adjacent to the proximal end 30 of the sleeve 24 and a second slot may be provided adjacent to the distal end 36 of the sleeve 24. It is contemplated that a dual sliding skive 414, 414' and/or dual slot arrangement may allow the physician to intraoperatively select the order of release of the threads 436, 438 in a manner similar to that described with respect to FIGS. 18-19 without actuation of the sliding skive 414. The materials that can be used for the various components of implants 10, 200 (and/or other medical devices disclosed herein including delivery devices 100, 300, 400) may include those commonly associated with medical devices. For simplicity purposes, the following discussion makes reference to implant 10, 200. However, this is not intended to limit the devices and methods described herein, as the discussion may be applied to other similar medical devices disclosed herein.

Implant 10, 200 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of implant 10, 200 may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of implant 10, 200 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of implant 10, 200 to achieve the same result.

In some embodiments, a degree of Magnetic Resonance Imaging (MM) compatibility is imparted into implant 10, 200. For example, implant 10, 200 or portions thereof, may be made of a material that does not substantially distort the image and create substantial artifacts (i.e., gaps in the image). Certain ferromagnetic materials, for example, may not be suitable because they may create artifacts in an MM image. Implant 10, 200 or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

Some examples of suitable polymers for implant 10, 200 may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

Those skilled in the art will appreciate that the different embodiments of the implant described here, their mode of operation, etc., are merely representative of the environment in which the present disclosure operates. Accordingly, a variety of alternatively shaped collaborating components may also be used as a substitutive for the purpose of engaging, steering and locating the stent at a desired target site, thus, not limiting the scope of the present disclosure. Further, the disclosed implants may be adequately stretchable, extendable, and retractable, allowing for its flexible deployment. More particularly, the configurations described here may be applicable for other medical applications as well, and accordingly, a variety of other medical devices may be used in combination with the implant. Those medical devices may include biopsy forceps, scissors, lithotripters, dilators, other cautery tools, and the like.

Further, while the implant is generally described along with an exemplary rigid and flexible region(s), a variety of other configurations and arrangements may also be contemplated and conceived as well. In addition, the operations, devices, and components, described herein may be equally applicable for other purposes where a component is required to be positioned in places where a leakage needs to be avoided or other treatments are desired. Embodiments of the present disclosure are thus applicable to medical and/or non-medical environments. Further, certain aspects of the aforementioned embodiments may be selectively used in collaboration, or removed, during practice, without departing from the scope of the disclosed embodiments.

Those skilled in the art will recognize that the present invention may be manifested in a variety of forms other than the specific embodiments described and contemplated herein. Accordingly, departure in form and detail may be made without departing from the scope and spirit of the present disclosure as described in the appended claims.

What is claimed is:

1. A delivery system for delivering an implant to a body lumen, the system comprising:
    an outer tubular member defining a lumen and having a proximal end region and a distal end region;
    an inner tubular member defining a lumen and having a proximal end region and a distal end region, the inner tubular member slidably disposed within the lumen of the outer tubular member and having at least one opening positioned in a side wall adjacent to the distal end region, the at least one opening extending from an outer surface to an inner surface of the inner tubular member;
    an expandable implant disposed about the outer surface of the inner tubular member adjacent the distal end region of the inner tubular member, the implant comprising at least a first rigid portion and a first flexible portion, the first flexible portion including a proximal end region, a distal end region, and a length extending therebetween; and
    a thread including a distal portion wrapped around an outer surface of the first flexible portion of the implant a plurality of times with the distal portion of the thread wrapped along the length of the first flexible portion of the implant, the thread configured to maintain the first flexible portion in a collapsed configuration;
    wherein the distal end region of the outer tubular member is disposed over the first rigid portion of the implant and is configured to maintain the first rigid portion in a radially collapsed configuration.

2. The delivery system of claim 1, wherein a distal end of the thread is positioned adjacent to the proximal end region of the first flexible portion and the thread is wrapped a plurality of times from the proximal end region to the distal end region of the first flexible portion.

3. The delivery system of claim 1, wherein a distal end of the thread is positioned adjacent to the distal end region of the first flexible portion and the thread is wrapped a plurality of times from the distal end region to the proximal end region of the first flexible portion.

4. The delivery system of claim 1, wherein a proximal portion of the thread extends into the lumen of the inner tubular member through the at least one opening and extends proximally to a proximal end configured to remain outside the proximal end region of the inner tubular member.

5. The delivery system of claim 4, further comprising a pulling member coupled to the proximal end of the thread.

6. The delivery system of claim 5, wherein the distal portion of the thread wrapped around the first flexible portion of the implant includes a plurality of releasable knots.

7. The delivery system of claim 1, wherein the first rigid portion comprises a self-expanding stent.

8. The delivery system claim 1, wherein the first flexible portion comprises a flexible membrane.

9. A delivery system for delivering an implant to a body lumen, the system comprising:
    an outer tubular member defining a lumen and having a proximal end region and a distal end region;
    an inner tubular member defining a lumen and having a proximal end region and a distal end region, the inner tubular member slidably disposed within the lumen of the outer tubular member and having a first proximal opening, a second opening distal to the first opening, a third opening distal to the second opening, and a fourth opening distal to the third opening, the first, second, third, and fourth openings positioned in a side wall adjacent to the distal end region and extending from an outer surface to an inner surface of the inner tubular member;

an expandable implant disposed about the outer surface of the inner tubular member adjacent the distal end region of the inner tubular member, the implant comprising a first rigid portion, a first flexible portion, a second rigid portion, and a second flexible portion; and a thread including a distal portion wrapped around the first flexible portion and the second flexible portion of the implant and configured to maintain the first and second flexible portions in a radially collapsed configuration;

wherein the distal portion of the thread wrapped around the first and/or second flexible portions of the implant includes a plurality of releasable knots;

wherein the distal end region of the outer tubular member is disposed over the first rigid portion and the second rigid portion of the implant and is configured to maintain the first and second rigid portions in a radially collapsed configuration.

10. The delivery system of claim 9, wherein the first flexible portion is positioned between the first rigid portion and the second rigid portion and a proximal end region of the second flexible portion is coupled to a distal end region of the second rigid portion.

11. The delivery system of claim 9, wherein the distal portion of the thread is configured to be woven in and out of the first, second, third and/or fourth openings such that the distal portion of thread is selectively wrapped around the first and second flexible portions.

12. The delivery system of claim 9, wherein a distal end of the thread is positioned adjacent to a proximal end region of the first flexible portion and the thread is wrapped from the proximal end region to a distal end region of the first flexible portion, enters the lumen of the inner tubular member through the second opening, exits the lumen of the inner tubular member through the third opening, is wrapped from a proximal end region to a distal end region of the second flexible portion, and re-enters the lumen of the inner tubular member through the fourth opening.

13. The delivery system of claim 9, wherein a distal end of the thread is positioned adjacent to a distal end region of the second flexible portion and the thread is wrapped from the distal end region to a proximal end region of the second flexible portion, enters the lumen of the inner tubular member through the third opening, exits the lumen of the inner tubular member through the second opening, is wrapped from a distal end region to a proximal end region of the first flexible portion, and re-enters the lumen of the inner tubular member through the first opening.

14. The delivery system of claim 9 wherein a proximal portion of the thread extends into the lumen of the inner tubular member through at least one of the first, second, third, or fourth openings and extends proximally to a proximal end configured to remain outside the proximal end region of the inner tubular member.

15. A delivery system for delivering an implant to a body lumen, the system comprising:

an outer tubular member defining a lumen and having a proximal end region and a distal end region;

an inner tubular member defining a lumen and having a proximal end region and a distal end region, the inner tubular member slidably disposed within the lumen of the outer tubular member;

an expandable implant disposed about the outer surface of the inner tubular member adjacent the distal end region of the inner tubular member, the implant comprising a self-expandable braided tubular stent frame having a proximal end and a distal end, the implant further including a flexible tubular sleeve extending distal of the distal end of the stent frame; and a thread including a distal portion wrapped around an outer surface of the flexible tubular sleeve a plurality of times to maintain the flexible tubular sleeve in a collapsed configuration;

wherein the distal end region of the outer tubular member is disposed over the stent frame of the implant to maintain the stent frame in a radially collapsed configuration.

16. The delivery system of claim 15, wherein the distal portion of the thread wrapped around the flexible tubular sleeve of the implant includes a plurality of releasable knots.

17. The delivery system of claim 16, wherein the distal portion of the thread wrapped around the flexible tubular sleeve can be selectively unraveled in a proximal-to-distal direction and a distal-to-proximal direction.

18. The delivery system of claim 16, wherein the inner tubular member includes an opening positioned in a side wall adjacent to the distal end region of the inner tubular member, the opening extending from an outer surface to an inner surface of the inner tubular member, wherein the thread extends through the opening with a proximal portion of the thread extending into the lumen of the inner tubular member.

19. The delivery system of claim 18, wherein the opening is located distal of the flexible tubular sleeve.

20. The delivery system of claim 18, wherein the opening is located proximal of the stent frame.

* * * * *